US012295733B2

(12) United States Patent
Clements et al.

(10) Patent No.: US 12,295,733 B2
(45) Date of Patent: May 13, 2025

(54) ELECTRODE-BASED SYSTEMS AND DEVICES FOR INTERFACING WITH BIOLOGICAL TISSUE AND RELATED METHODS

(71) Applicant: BioCircuit Technologies, Inc., Atlanta, GA (US)

(72) Inventors: Isaac Perry Clements, Marietta, GA (US); Anna Harrison, Atlanta, GA (US); Edgar Brown, Decatur, GA (US); Amanda Preyer, Atlanta, GA (US); James David Ross, Decatur, GA (US); Andrew Willsie, Lilburn, GA (US); Maximilian Sonntag, Atlanta, GA (US)

(73) Assignee: BioCircuit Technologies, Inc., Atlanta, GA (US)

(*) Notice: Subject to any disclaimer, the term of this patent is extended or adjusted under 35 U.S.C. 154(b) by 0 days.

(21) Appl. No.: 18/187,456

(22) Filed: Mar. 21, 2023

(65) Prior Publication Data
US 2023/0380743 A1     Nov. 30, 2023

Related U.S. Application Data

(63) Continuation of application No. 16/673,734, filed on Nov. 4, 2019, now Pat. No. 11,612,344.
(Continued)

(51) Int. Cl.
*A61B 5/00*      (2006.01)
*A61B 5/0536*      (2021.01)
*A61B 5/24*      (2021.01)

(52) U.S. Cl.
CPC .............. *A61B 5/24* (2021.01); *A61B 5/0536* (2013.01); *A61B 5/6833* (2013.01);
(Continued)

(58) Field of Classification Search
CPC ....... A61B 5/24; A61B 5/0536; A61B 5/6833; A61B 5/6843; A61B 5/7203;
(Continued)

(56) References Cited

U.S. PATENT DOCUMENTS

| 4,665,499 A | * | 5/1987 | Zacharski | A61B 5/377 702/191 |
| 5,615,687 A | | 4/1997 | Pritchard | |

(Continued)

FOREIGN PATENT DOCUMENTS

| EP | 2056714 A2 | 5/2009 |
| EP | 3185951 A2 | 7/2017 |

(Continued)

OTHER PUBLICATIONS

Guermandi, M. et al. "A driving right leg circuit (DgRL) for improved common mode rejection in bio-potential acquisition systems." IEEE transactions on biomedical circuits and systems 10.2 (2015): 507-517.

*Primary Examiner* — May A Abouelela
(74) *Attorney, Agent, or Firm* — Meunier Carlin & Curfman LLC

(57) ABSTRACT

Systems, devices, and methods for interfacing with biological tissue are described herein. An example electrode patch as described herein includes a flexible substrate and an electrode array arranged on the flexible substrate. The electrode array includes a plurality of electrodes, where each of the plurality of electrodes is formed of a hydrogel. Additionally, each of the plurality of electrodes defines a raised geometry. Additionally, an example system includes the electrode patch, which is configured to interface with a subject's skin, and an electronics module operably coupled to the electrode array.

15 Claims, 20 Drawing Sheets

Related U.S. Application Data

(60) Provisional application No. 62/755,268, filed on Nov. 2, 2018.

(52) U.S. Cl.
CPC .......... *A61B 5/6843* (2013.01); *A61B 5/7203* (2013.01); *A61B 2562/046* (2013.01); *A61B 2562/164* (2013.01)

(58) Field of Classification Search
CPC ........ A61B 2562/046; A61B 2562/164; A61B 5/296; A61B 5/30; A61B 2562/0209; A61B 2562/125; A61B 2562/166; A61B 2562/227; A61B 5/6824; A61B 5/4041; A61N 1/36003; A61N 1/36014; A61N 1/36031
See application file for complete search history.

(56) References Cited

U.S. PATENT DOCUMENTS

| | | | |
|---|---|---|---|
| 5,961,484 A * | 10/1999 | Gusakov | A61B 5/263 600/394 |
| 5,976,094 A | 11/1999 | Gozani | |
| 6,266,558 B1 | 7/2001 | Gozani et al. | |
| 6,394,953 B1 | 5/2002 | Devlin et al. | |
| 6,526,303 B1 * | 2/2003 | Scampini | A61N 1/0492 600/386 |
| 6,556,861 B1 * | 4/2003 | Prichep | A61B 5/7203 607/45 |
| 7,396,976 B2 * | 7/2008 | Hurwitz | A61F 13/0203 602/41 |
| 7,532,921 B2 * | 5/2009 | Eichler | A61B 5/0536 600/397 |
| 8,029,313 B2 | 10/2011 | Fendrock et al. | |
| 8,897,853 B2 | 11/2014 | Aziz et al. | |
| 9,332,918 B1 * | 5/2016 | Buckley | A61B 5/24 |
| 9,656,070 B2 | 5/2017 | Gozani et al. | |
| 10,067,117 B2 | 9/2018 | Tyler et al. | |
| 10,173,060 B2 * | 1/2019 | Wong | A61N 1/0484 |
| 10,420,480 B1 * | 9/2019 | Schermerhorn | A61B 5/24 |
| 10,463,854 B2 * | 11/2019 | Perez | A61B 5/369 |
| 10,765,859 B2 * | 9/2020 | Bouton | A61B 5/686 |
| 10,994,130 B2 * | 5/2021 | Clements | A61B 5/24 |
| 2002/0016548 A1 * | 2/2002 | Stadler | A61B 5/358 600/509 |
| 2003/0088167 A1 | 5/2003 | Fendrock et al. | |
| 2003/0144710 A1 * | 7/2003 | Haugland | A61F 2/72 607/48 |
| 2004/0243017 A1 * | 12/2004 | Causevic | A61B 5/372 600/544 |
| 2005/0101878 A1 * | 5/2005 | Daly | A61N 1/36038 600/554 |
| 2006/0276702 A1 * | 12/2006 | McGinnis | A61B 5/296 600/372 |
| 2006/0276720 A1 * | 12/2006 | McGinnis | A61B 5/296 600/557 |
| 2007/0244410 A1 * | 10/2007 | Fridman | A61B 5/24 600/554 |
| 2007/0282217 A1 * | 12/2007 | McGinnis | A61B 5/395 600/554 |
| 2008/0051673 A1 * | 2/2008 | Kong | A61B 5/6825 600/546 |
| 2008/0234781 A1 * | 9/2008 | Einav | A61N 1/36031 607/48 |
| 2009/0005667 A1 | 1/2009 | Cui et al. | |
| 2010/0010369 A1 * | 1/2010 | Pomfrett | A61B 5/0536 600/554 |
| 2010/0152600 A1 * | 6/2010 | Droitcour | A61B 5/7221 600/534 |
| 2011/0046473 A1 * | 2/2011 | Pradeep | A61B 5/16 600/413 |
| 2011/0105939 A1 * | 5/2011 | Yong | A61B 5/4041 600/554 |
| 2012/0123220 A1 * | 5/2012 | Iyer | A61L 15/58 156/767 |
| 2012/0123232 A1 * | 5/2012 | Najarian | G16Z 99/00 600/407 |
| 2012/0209102 A1 | 8/2012 | Ylotalo et al. | |
| 2013/0060184 A1 * | 3/2013 | Rea | A61F 13/0246 602/54 |
| 2014/0018872 A1 * | 1/2014 | Siejko | A61N 1/371 607/11 |
| 2015/0216483 A1 * | 8/2015 | Sevcencu | A61B 5/7278 600/301 |
| 2015/0224308 A1 * | 8/2015 | Ichimura | A61N 1/36003 600/595 |
| 2015/0289931 A1 * | 10/2015 | Puryear | A61B 18/1492 606/41 |
| 2015/0313498 A1 * | 11/2015 | Coleman | A61B 5/38 600/383 |
| 2016/0113540 A1 * | 4/2016 | Chi | A61B 5/6843 600/509 |
| 2016/0228691 A1 | 8/2016 | Mathew et al. | |
| 2016/0270679 A1 * | 9/2016 | Mahon | A61B 5/7225 |
| 2016/0331326 A1 * | 11/2016 | Xiang | A61B 5/24 |
| 2017/0080207 A1 | 3/2017 | Perez et al. | |
| 2017/0224990 A1 | 8/2017 | Goldwasser et al. | |
| 2017/0245776 A1 * | 8/2017 | Kurtz | A61B 5/7203 |
| 2017/0245797 A1 * | 8/2017 | Quinn | A61B 5/6833 |
| 2017/0273633 A1 * | 9/2017 | Saumarez | A61B 5/349 |
| 2018/0014780 A1 * | 1/2018 | Sotzing | A61B 5/25 |
| 2018/0020931 A1 * | 1/2018 | Shusterman | A61N 1/3627 600/483 |
| 2018/0047228 A1 * | 2/2018 | Hyde | G16H 40/20 |
| 2018/0064377 A1 * | 3/2018 | Rogers | B01L 3/5027 |
| 2018/0078210 A1 * | 3/2018 | Snow | A61B 5/316 |
| 2018/0092600 A1 * | 4/2018 | Simons | A61N 1/36031 |
| 2018/0125689 A1 | 5/2018 | Perez et al. | |
| 2018/0146927 A1 * | 5/2018 | Melman | A61B 5/686 |
| 2018/0177459 A1 * | 6/2018 | Eletr | A61B 5/02125 |
| 2018/0177996 A1 * | 6/2018 | Gozani | A61B 5/4806 |
| 2018/0184735 A1 | 7/2018 | Longinotti-Buitoni et al. | |
| 2018/0184939 A1 * | 7/2018 | Christiansen | A61B 5/6833 |
| 2018/0185645 A1 * | 7/2018 | Vallejo | A61N 1/0556 |
| 2018/0193647 A1 | 7/2018 | Yang et al. | |
| 2018/0318574 A1 * | 11/2018 | Makkiabadi | A61B 5/316 |
| 2019/0001129 A1 | 1/2019 | Rosenbluth et al. | |
| 2019/0262606 A1 * | 8/2019 | Masuda | A61B 5/202 |
| 2020/0071648 A1 * | 3/2020 | Moore | A61N 1/18 |
| 2020/0121206 A1 * | 4/2020 | Dumont | A61B 5/30 |
| 2020/0329992 A1 * | 10/2020 | Gerhardt | A61B 5/6843 |
| 2020/0330011 A1 * | 10/2020 | Honore | A61B 5/1455 |
| 2020/0393438 A1 * | 12/2020 | Wijdenes | A61B 5/291 |
| 2020/0397314 A1 * | 12/2020 | Vaussenat | A61B 5/02055 |
| 2021/0205619 A1 * | 7/2021 | Wong | A61N 1/36007 |
| 2021/0402182 A1 | 12/2021 | Kendall et al. | |
| 2022/0062621 A1 | 3/2022 | Hogg et al. | |

FOREIGN PATENT DOCUMENTS

| | | |
|---|---|---|
| RU | 2658452 C2 | 10/2017 |
| WO | 2008024137 A1 | 2/2008 |
| WO | 2008024137 A2 | 2/2008 |
| WO | 2016032929 A1 | 3/2016 |
| WO | 2016032929 A2 | 3/2016 |

* cited by examiner

ELECTRODE-BASED SYSTEMS AND DEVICES FOR INTERFACING WITH BIOLOGICAL TISSUE AND RELATED METHODS

CROSS-REFERENCE TO RELATED APPLICATIONS

This application is a continuation of U.S. patent application Ser. No. 16/673,734, filed Nov. 4, 2019, which claims the benefit of and priority to U.S. Provisional Patent App. No. 62/755,268, filed on Nov. 2, 2018, both of which are incorporated herein by reference in their entireties.

STATEMENT REGARDING FEDERALLY FUNDED RESEARCH

This invention was made with government support under Grant No. 2R44NS065545 awarded by the National Institutes of Health—National Institute of Neurological Disorders and Stroke. The government has certain rights in the invention.

BACKGROUND

A variety of clinical and non-clinical situations call for electrical interfacing with biological tissues, especially electroactive tissues such as nerve and muscle. For example electrodiagnostic studies can be performed to assess neuromuscular function for the purpose of diagnosing peripheral nerve and muscle pathologies. Similar paradigms for stimulating or recording from tissues can also be used for other testing methods or for therapeutic effect.

In electrodiagnostics, traditional nerve conduction studies are typically performed by placing two sets of large area electrodes on the skin overlying a nerve, one for recording and one for stimulation. In the case of motor studies, the recording electrodes are typically placed over a muscle innervated by the nerve rather than the nerve itself. Current pulses are then passed through the stimulating electrodes, leading to depolarization of underlying nerves. This depolarization propagates along the nerve in both directions. When the wave of depolarization passes through the tissue underlying the recording electrodes, the electrode records a generated voltage that is then analyzed. Two measurements commonly used in traditional nerve conduction studies are the response amplitude and the conduction velocity. The response amplitude can be reduced in cases of axonal loss. The conduction velocity can be reduced as a result of diseases or conditions resulting in demyelination.

Conventional tests use several flat metal or gel disc electrodes that can be interfaced with the skin with conductive gel or adhesive. Several electrical shocks are delivered to the nerve, often through a pair of metal electrodes fixed to the body or contacted to the body through a hand-held device. The delay and amplitude of the evoked response are recorded. Though a skilled and experienced operator conducts these procedures, differences in individual anatomy make it difficult to accurately position the electrodes. As a result, the electrodes must often be repositioned to optimize the recorded response. At the conclusion of the test, the operator has a differential measurement of a single location on the nerve or muscle being tested.

Despite operator effort to place the stimulating and recording electrodes as close to the course of the target nerve as possible, anatomic variability can cause unavoidable errors in electrode positioning. With regard to the stimulating electrodes, positioning errors can cause an increase in the electrical current required to deliver an adequate stimulus to the nerve under test, leading to patient discomfort and unintentional stimulation of adjacent nerves. With regard to recording electrodes, positioning errors can cause artifacts such as baseline deflections and reductions in maximal amplitude. In clinical practice, placement errors can be minimized by using stimulus and recording sites having minimal anatomic variability and ensuring the test is conducted by a trained operator capable of recognizing placement error artifacts and adjusting electrode positions to minimize them.

Optimally configured stimulating electrodes would be able to deliver current to the target tissue while minimizing unintentional stimulation of the surrounding tissue. Optimally configured recording electrodes, e.g. positioned directly over the nerve of interest, would maximize the recorded signal relative to unwanted signal or noise. Simply increasing electrode size, thereby increasing the chance that the nerve lays directly underneath some portion of the electrode, is not an effective mechanism for reducing placement error. In the case of stimulating electrodes, larger active sites stimulate a large volume of underlying tissue, reducing stimulation selectivity. A larger total current is required to depolarize both the underlying target tissue as well the surrounding non-target tissue. In the case of recording electrodes, a larger active site will measure from an increased the volume of tissue, and sensitivity to signals from a relatively small portion of target tissue will be reduced.

SUMMARY

An example electrode patch is described herein. The electrode patch includes a flexible substrate and an electrode array arranged on the flexible substrate. The electrode array includes a plurality of electrodes, where each of the plurality of electrodes is formed of a hydrogel. Additionally, each of the plurality of electrodes defines a raised geometry.

The raised geometry is configured to closely contact or push into a patient's skin. For example, in some implementations, the raised geometry has a dome-like, convex, cylindrical, pyramidal, or cone-like shape.

In some implementations, each of the electrodes is attached to the flexible substrate. For example, each of the electrodes includes an electrode contact, where the electrode contact is printed on the flexible substrate. The hydrogel of each of the electrodes is molded onto the electrode contact.

In some implementations, the electrode array includes at least two independently addressable electrodes. Alternatively or additionally, the electrode array includes at least three electrodes.

In some implementations, the electrode patch further includes an adhesive layer arranged on at least a portion of the flexible substrate.

In some implementations, the electrode patch further includes an intermediate layer arranged on the flexible substrate. The intermediate layer is optionally made of compressible-foam, rubber or silicone. Alternatively or additionally, the intermediate layer optionally includes a plurality of openings, where each respective opening corresponds to one of the plurality of electrodes.

In some implementations, at least a portion of the flexible substrate or the intermediate layer is configured to adhere to a patient's skin.

In some implementations, the electrode patch further includes an adhesive layer arranged on at least a portion of the intermediate layer.

In some implementations, the flexible substrate or the intermediate layer is made from an elastic material.

In some implementations, the intermediate layer includes at least one groove or cutout. Alternatively or additionally, the flexible substrate includes at least one groove or cutout.

In some implementations, at least a portion of the electrode patch is translucent or transparent.

In some implementations, the plurality of electrodes are arranged in a grid. For example, the grid has a square, rectangular, or hexagonal shape.

In some implementations, the plurality of electrodes are arranged in a circle, semi-circular, or arc pattern.

In some implementations, the plurality of electrodes are unevenly distributed.

In some implementations, the electrode array includes a first group of electrodes and a second group of electrodes. Optionally, the arrangement of the first group of electrodes is different than the arrangement of the second group of electrodes. Alternatively or additionally, the first group of electrodes is optionally configured as a cathode and the second group of electrodes is optionally configured as an anode. Alternatively or additionally, the first group of electrodes is optionally configured for stimulation and the second group of electrodes is optionally configured for recording.

In some implementations, the electrode patch further includes a compression pad configured to apply pressure to the electrode array. Optionally, the compression pad includes a rigid member, where the rigid member is configured to focus the pressure onto the electrode array. The rigid member is optionally configured to focus the pressure onto a portion of the electrode array and/or onto one or more electrodes of the electrode array. Alternatively or additionally, the rigid member includes at least one groove.

In some implementations, the electrodes of the electrode array are individually addressable. Alternatively or additionally, the electrode patch further includes a plurality of traces, where each of the traces extends between a respective electrode and a peripheral region of the electrode patch.

An example system is also described herein. The system includes an electrode patch configured to interface with a subject's skin, where the electrode patch includes an electrode array including a plurality of electrodes. The system also includes an electronics module operably coupled to the electrode array. The electronics module is configured to deliver a stimulus to an electroactive tissue via the electrode array, or record an evoked electrical response from the electroactive tissue via the electrode array. Optionally, the electronics module is configured to both deliver the stimulus to the electroactive tissue via the electrode array and record the evoked electrical response from the electroactive tissue via the electrode array.

In some implementations, the electronics module is further configured to use the recorded evoked electrical response to adjust the stimulus delivered to the electroactive tissue.

In some implementations, the electroactive tissue is a nerve.

In some implementations, the electronics module is further configured to independently address each of the plurality of electrodes.

In some implementations, the electronics module is further configured to deliver a plurality of successive stimuli to the electroactive tissue via the electrode array with precise timing. For example, the plurality of successive stimuli are delivered precisely in phase or out of phase with other signals.

In some implementations, the electronics module is further configured to cancel noise by averaging the plurality of successive stimuli. For example, the plurality of successive stimuli is two stimuli.

In some implementations, the electronics module comprises a modified driven right leg circuit configured to measure the subject's common-mode, and force a ground of the electronics module to the subject's common-mode.

In some implementations, the electronics module is further configured for functional nerve imaging.

In some implementations, the electronics module is further configured for a nerve conduction study.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 14A illustrates an implementation where traces and contact pads arranged on the flexible substrate are wrapped around another substrate. FIG. 14B illustrates an implementation where traces and contact pads arranged on the flexible substrate are folded over.

FIG. 16A illustrates spatial activity mapping. FIG. 16B is a still frame of signal propagation through the patient's median nerve.

DETAILED DESCRIPTION

Figure 1:
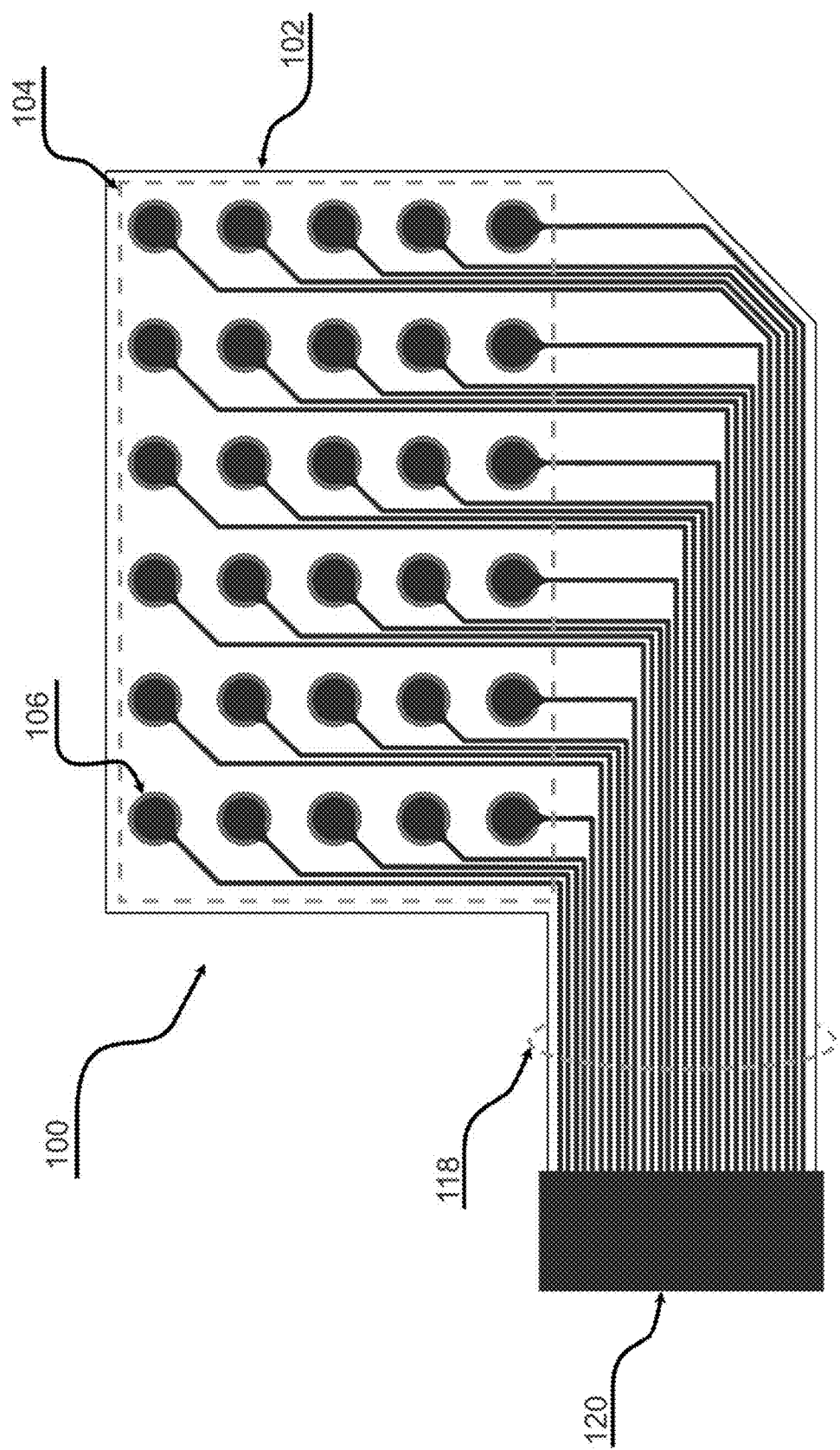
FIG. 1 illustrates an example electrode patch according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Referring now to FIGS. 1-10B, an example electrode patch 100 is described. The electrode patch 100 includes a flexible substrate 102 and an electrode array 104 arranged on the flexible substrate 102. This disclosure contemplates that the flexible substrate 102 can be formed from an elastic material and/or material that increases patient comfort. For example, the flexible substrate 102 can be formed from materials including, but not limited to, silicone, polyimide, polyethylene terephthalate, liquid crystal polymer, fluoropolymers such as polyvinylidene fluoride or polyvinylidene difluoride (PVDF), urethanes, polyurethanes, or thermoplastic polyurethanes. It should be understood that the materials above are provided only as examples and that the flexible substrate 102 can be formed from other materials.

The electrode array 104 includes a plurality of electrodes 106, where each of the electrodes 106 is formed, at least partially, from a hydrogel. A hydrogel is a three-dimensional (3D) solid formed by a network of cross-linked polymers dispersed in a liquid such as water. The liquid (e.g., water) is held within the polymer structure. Additionally, the hydrogel that forms the electrodes 106 is conductive, for example, by ionic conductivity or by including conductive fillers (e.g., metallic particles, conductive polymers, carbon-based material) in the hydrogel. In other words, the hydrogel that forms the electrodes 106 is an electrically-conductive hydrogel. Hydrogel offers advantages over other electrode materials (e.g., metal) including, but not limited to, being soft, chemically tunable, biocompatible, and ionically conductive, and amenable to cost-effective manufacturing (e.g. can be dispensed in fluid form). As described below, the hydrogel is moldable or castable, e.g., the hydrogel is solidified enough to maintain its shape. Hydrogels are known in the art and are therefore not described further. Hydrogel electrodes have been used in medial applications such as electroencephalography (EEG) and electrocardiography (ECG). Although electrodes formed from a hydrogel are provided as examples herein, this disclosure contemplates that the electrodes may be formed of other materials including, but not limited to, other gels such as conductive organogel or xerogel.

The hydrogel of each of the electrodes 106 is attached (e.g., fixed, bonded, etc.) to the flexible substrate 102. This is shown in FIGS. 3A-3D, for example. It should be understood that attaching hydrogel electrodes to the flexible substrate 102 is different than merely providing a hydrogel on a surface, where the hydrogel clings to the surfaces via surface tension. In other words, the hydrogel electrodes are attached to the flexible substrate 102 during the manufacturing process. For example, electrode contacts 106A and traces (described below) are fabricated onto the flexible substrate 102. In some implementations, the electrode contacts and/or traces are optionally screen-printed onto the flexible substrate 102. In these implementations, the electrode contacts and/or traces are formed from conductive inks such as silver (Ag) or silver chloride (AgCl) ink. In other implementations, the electrode contacts and/or traces are disposed through standard microfabrication processes, such those including photolithography. In either implementation, the electrode contacts and/or traces are therefore flat and/or thin conductive structures, which is in contrast to bulk metallic or conductive structures. Thereafter, the hydrogel 106B, which is moldable or castable, is provided onto the electrode contact 106A. The hydrogel 106B can be molded or casted into the desired shape (described below). The electrode, which includes an electrode contact 106A and hydrogel 106B, is labeled with reference number 106 in the figures. The electrodes 106 are therefore fixed or bonded to the flexible substrate 102. In particular, the hydrogel 106B is fixed or bonded to at least a portion of the flexible substrate 102, the electrode contact 106A, and/or an intermediate layer (described below).

Figure 3A:
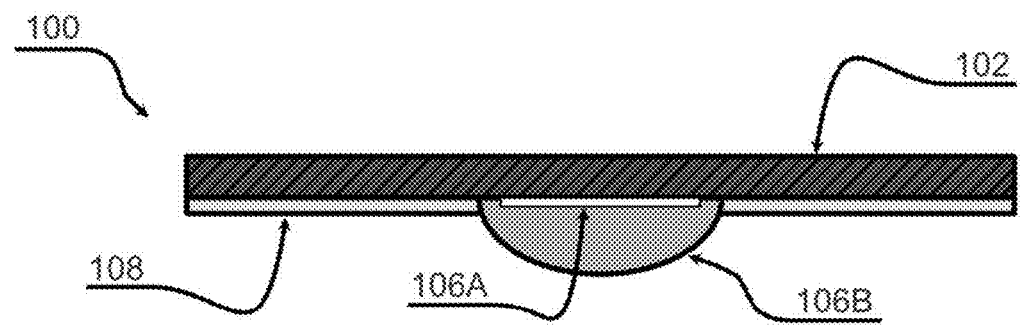
FIGS. 3A-3C are cross-sectional views of a portion of an electrode patch according to implementations described herein. The electrode patch of FIG. 3A includes an adhesive layer. The electrode patch of FIG. 3B includes adhesive and intermediate layers. The electrode patch of FIG. 3C includes an intermediate layer.
Figure 3B:
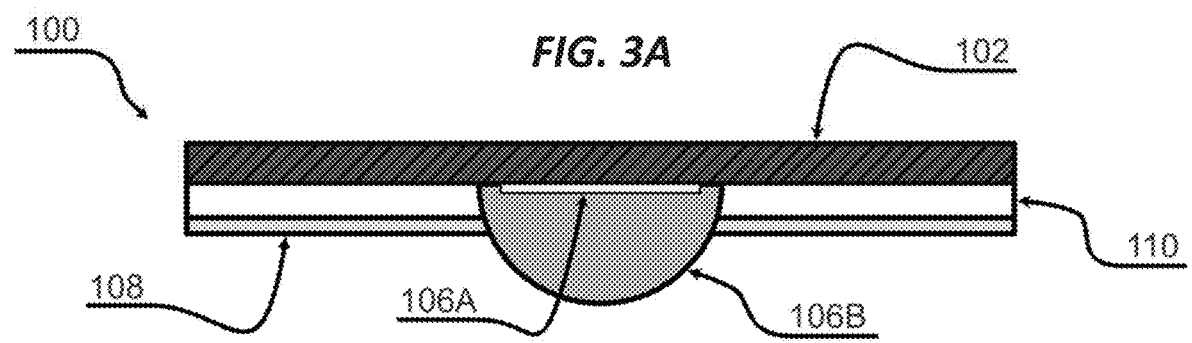
Figure 3C:
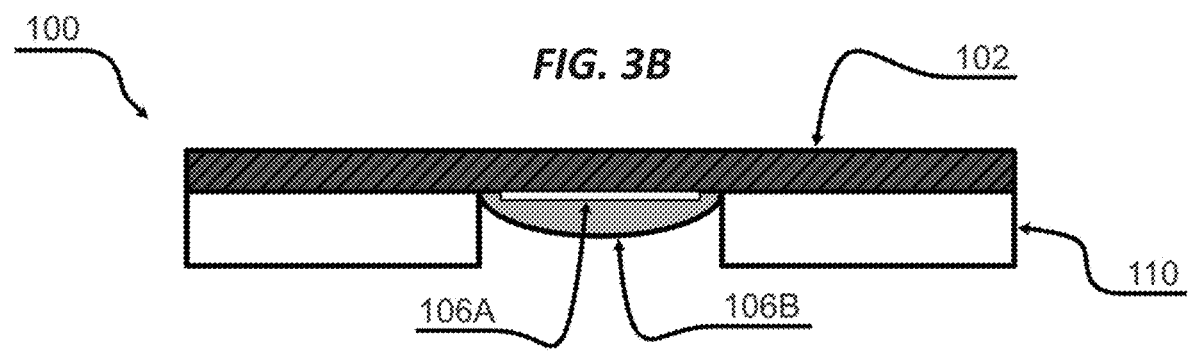
Figure 3D:
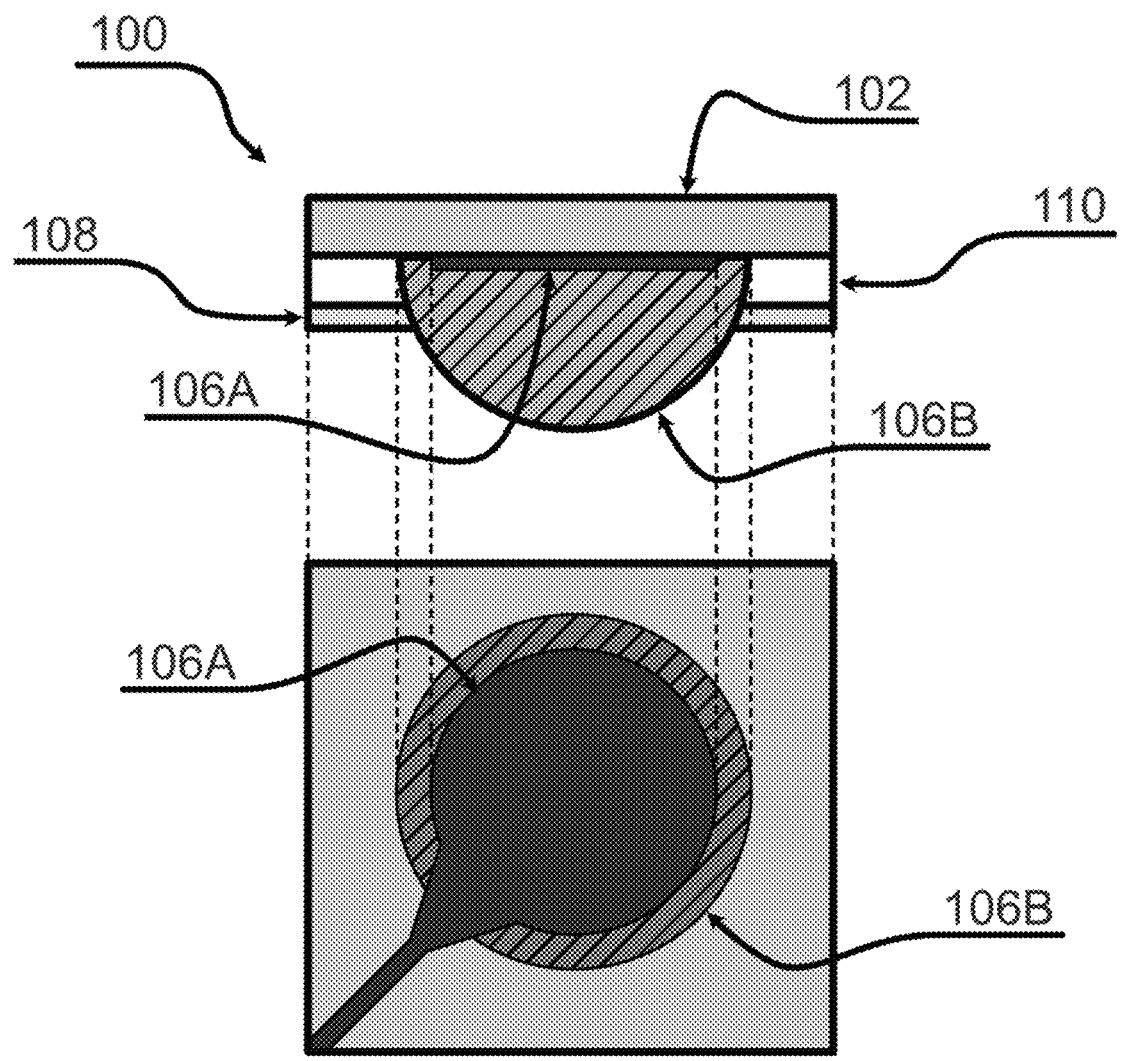
FIG. 3D are cross-sectional and plan views shown an electrode in the electrode patch of FIG. 3B.

As shown in FIGS. 3A, 3B, and 3D, each of the plurality of electrodes 106 defines a raised geometry. In FIGS. 3A, 3B, and 3D, the electrodes 106 have the raised geometry with respect to the flexible substrate 102, as well as any other layers arranged in the flexible substrate 102 such as adhesive and/or intermediate layers, because the hydrogel 106B extends above the flexible substrate 102 (and adhesive and/or intermediate layers if present). As shown in the figures, the hydrogel 106B extends above all of the layers and makes direct contact with the patient's skin. In other words, the electrodes 106 have a raised geometry with respect to the layer configured to contact a patient's skin. The hydrogel 106B therefore "sticks out" and makes direct contact with the patient's skin. There is no material and/or layer arranged between the hydrogel 106B and the patient's skin. For example, the electrodes 106 having the raised geometry are configured to closely contact or push into the patient's skin (see e.g., FIGS. 9A and 9B). This is also in contrast to the implementation shown in FIG. 3C, where the hydrogel 106B does not extend beyond the intermediate layer, which is the layer configured to contact the patient's skin. In some implementations, the raised geometry has a dome-like, convex, cylindrical, pyramidal, or cone-like shape. It should be understood that dome-like, convex, cylindrical, pyramidal, or cone-like shapes are provided only as examples and that other geometries that result in close contact with and/or push into the patient's skin can be used. This disclosure contemplates that each of the electrodes 106 can extend above the flexible substrate 102 (and adhesive and/or intermediate layers if present) by about the same amount as the diameter. As described herein, the diameter of each of the electrodes 106 may be between about several millimeters (e.g., 2-3 mm) and about 1 cm (e.g., 2.00 mm, 2.01 mm, 2.02 mm . . . 0.98 cm, 0.99 cm, 1.00 cm) and any value or range therebetween. Thus, as one example, an electrode with 0.5 cm diameter may extend about 0.5 cm above the flexible substrate 102 (and adhesive and/or intermediate layers if present). It should be understood that 0.5 cm is provided only as example. As shown in FIGS. 3A, 3B, and 3D, the electrodes 106 are prominent, dome-like shapes. In particular, the edge of the hydrogel 106B slopes sharply upward from the flexible substrate 102 and then gradually reduces slope as it approaches the apex. This ensures that the hydrogel 106B, which is attached to a relatively small electrode contact 106A (e.g., between ~2 mm and 1 cm diameter), "sticks out" relative to the flexible substrate 102 (and adhesive and/or intermediate layers if present). As described above, the hydrogel can be molded or casted to form the raised geometry. The raised geometry facilitates creation of an intimate, stable interface between the hydrogel 106B and the skin surface, improving stimulation and/or recording characteristics. The direct contact of hydrogel 106B with the skin can also reduce motion artifacts during measurements. As noted above, there is no material arranged between the hydrogel 106B and the patient's skin. It should be understood that the sizes of the electrodes 106 described herein are provided only as examples and that the electrode 106 can have other sizes.

Additionally, as shown in FIGS. 3A-3D, the electrode patch 100 can further include an adhesive layer 108 and/or an intermediate layer 110. The adhesive layer 108 and/or the intermediate layer 110 are arranged between the electrode patch 100 and the patient when applied to the patient's skin (see e.g., FIGS. 6, 9A, and 9B). This disclosure contemplates that the adhesive layer 108 and/or the intermediate layer 110 can cover one or more portions, whether contiguous or non-contiguous portions, of the flexible substrate 102. The adhesive layer 108 can be any material configured to stick to a patient's skin including, but not limited to, acrylic adhesive. Similar to the flexible substrate 102, the intermediate layer 110 can be an elastic material and/or material that increases patient comfort. For example, the intermediate layer 110 can be made of compressible-foam, rubber or silicone. Optionally, the intermediate layer 110 can be made of a low adhesive or slightly tacky material (e.g., tacky silicone), which sticks to, but easily peels away from, the patient's skin. It should be understood that the materials above are provided only as examples and that the adhesive layer 108 and/or the intermediate layer 110 can be formed from other materials. In FIG. 3A, the adhesive layer 108 is arranged on the flexible substrate 102. In FIG. 3B, the intermediate layer 110 is arranged on the flexible substrate 102, and the adhesive layer 108 is arranged on the intermediate layer 110. In FIG. 3C, the intermediate layer 110 is arranged on the flexible substrate 102. In FIG. 3C, the hydrogel 106B of the electrode 106 is below the intermediate layer 110, which is in contrast to the design of FIGS. 3A and 3B. The electrode 106 in FIG. 3C therefore does not have a "raised geometry" like the electrodes shown in FIGS. 3A and 3B. In the implementation of FIG. 3C, the electrode patch 100 is attached to the patient's skin via suction. Thus, there is less motivation to provide an adhesive layer. Additionally, as shown in FIGS. 3B and 3C, the adhesive layer 108 and/or the intermediate layer 110 include a plurality of openings 112, where each respective opening 112 corresponds to one of the plurality of electrodes 106. In other words, the adhesive layer 108 and/or the intermediate layer 110 are not provided over the electrodes 106.

Figures 7A, 7B:
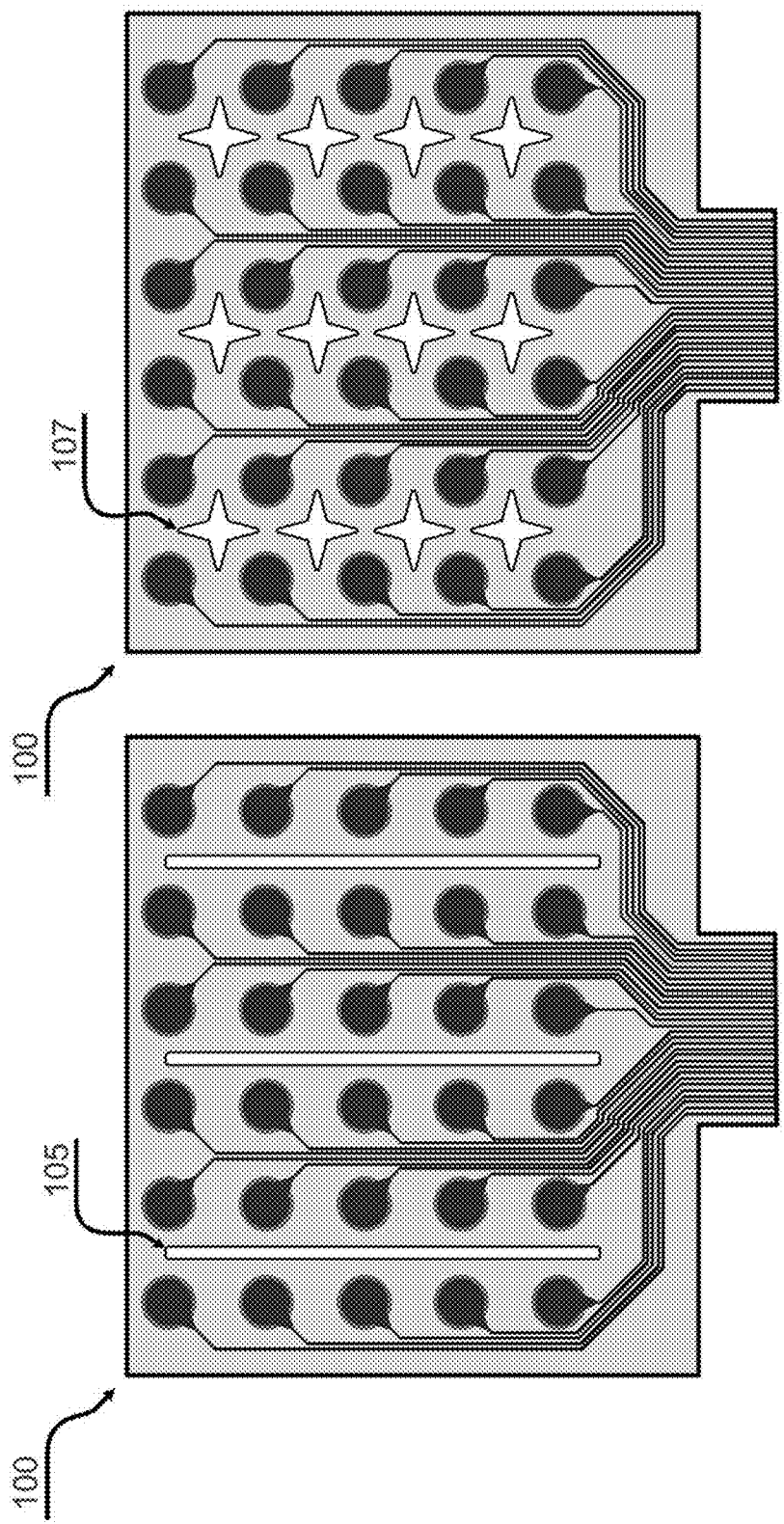
FIGS. 7A and 7B illustrate electrode patches according to implementations described herein. The electrode patch of FIG. 7A includes a plurality of grooves. The electrode patch of FIG. 7B includes a plurality of cutouts.
Figure 8:
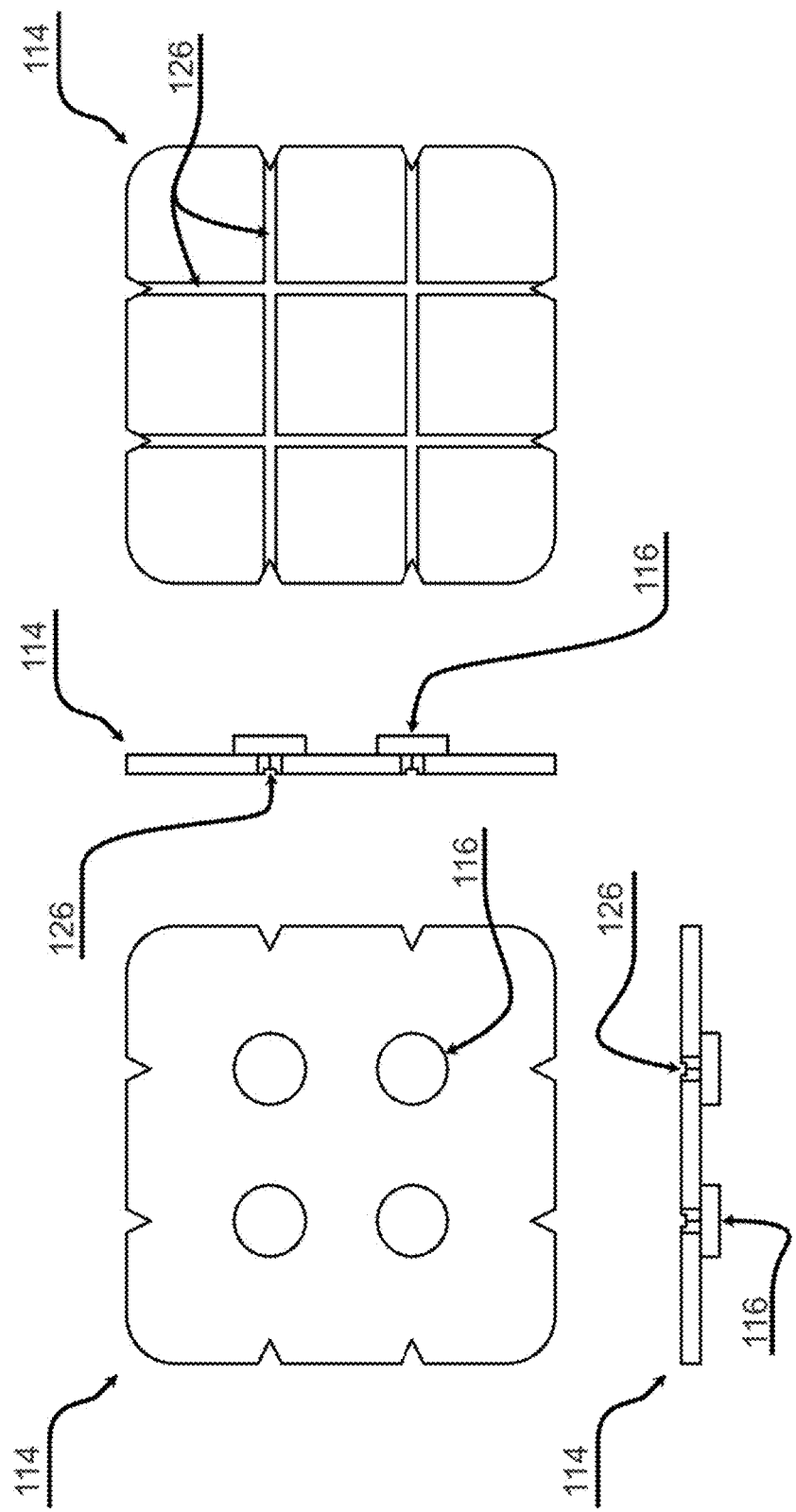
FIG. 8 illustrates an example compression pad of an electrode patch according to implementations described herein.
Figures 9A, 9B:
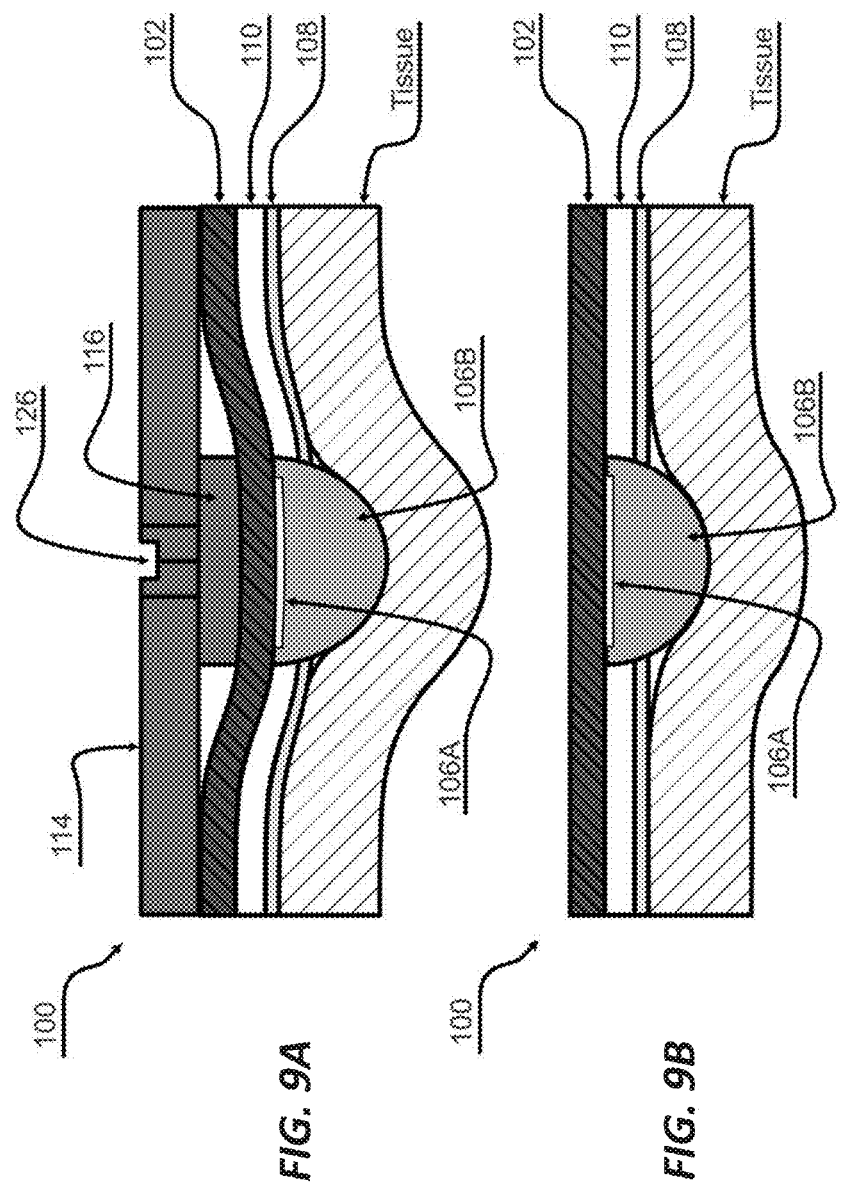
FIGS. 9A and 9B illustrate an electrode patch applied to a patient according to implementations described herein. The electrode patch of FIG. 9A includes a compression pad, which is in contrast to the electrode patch of FIG. 9B.

As shown in FIGS. 7A and 7B, the electrode patch 100 can include at least one elongate cutout 105 (FIG. 7A) or at least one cutout 107 (FIG. 7B). The elongate cutout 105 and/or cutouts 107 can be provided in the flexible substrate and/or the intermediate layer of the electrode patch. The cutouts act as relief cuts, increasing flexibility or conformability of the electrode patch 100. Additionally, the cutouts are windows in the electrode patch 100 which allow the patient and/or medical personnel see the underlying anatomical structure. Elongate cutouts 105 act as relief cuts, increasing flexibility or conformability of the electrode patch 100. Elongate cutouts 105 also facilitate visibility of the underlying anatomical structure during placement of the electrode patch 100. Cutouts 107 act as relief cuts, increasing flexibility or conformability of the electrode patch 100 and also facilitate visibility of the underlying anatomical structure during placement of the electrode patch 100. Optionally, both elongate 105 and cutouts 107 can be provided in the same electrode patch 100. It should be understood that the number, sizes, shapes, and/or arrangement of the elongate cutouts 105 in FIG. 7A and cutouts 107 in FIG. 7B are provided only as examples. This disclosure contemplates providing more or less cutouts than shown in the figures, as well as cutouts having other sizes, shapes, and/or arrangements than shown in the figures. Alternatively or additionally, this disclosure contemplates providing one or more grooves (e.g., similar to those provided in the rigid member as shown in FIGS. 8 and 9A) in the flexible substrate and/or the intermediate layer of the electrode patch. Alternatively or additionally, at least a portion of the electrode patch 100 is optionally translucent or transparent. This facilitates visibility of the underlying anatomical structure during placement of the electrode patch 100. In some implementations, the entire electrode patch 100 is translucent or transparent. In other implementations, only a portion of the electrode patch 100 is translucent or transparent. This can be accomplished by using translucent or transparent materials for the flexible substrate, intermediate layer, and/or adhesive layer of the electrode patch 100.

Figure 2:
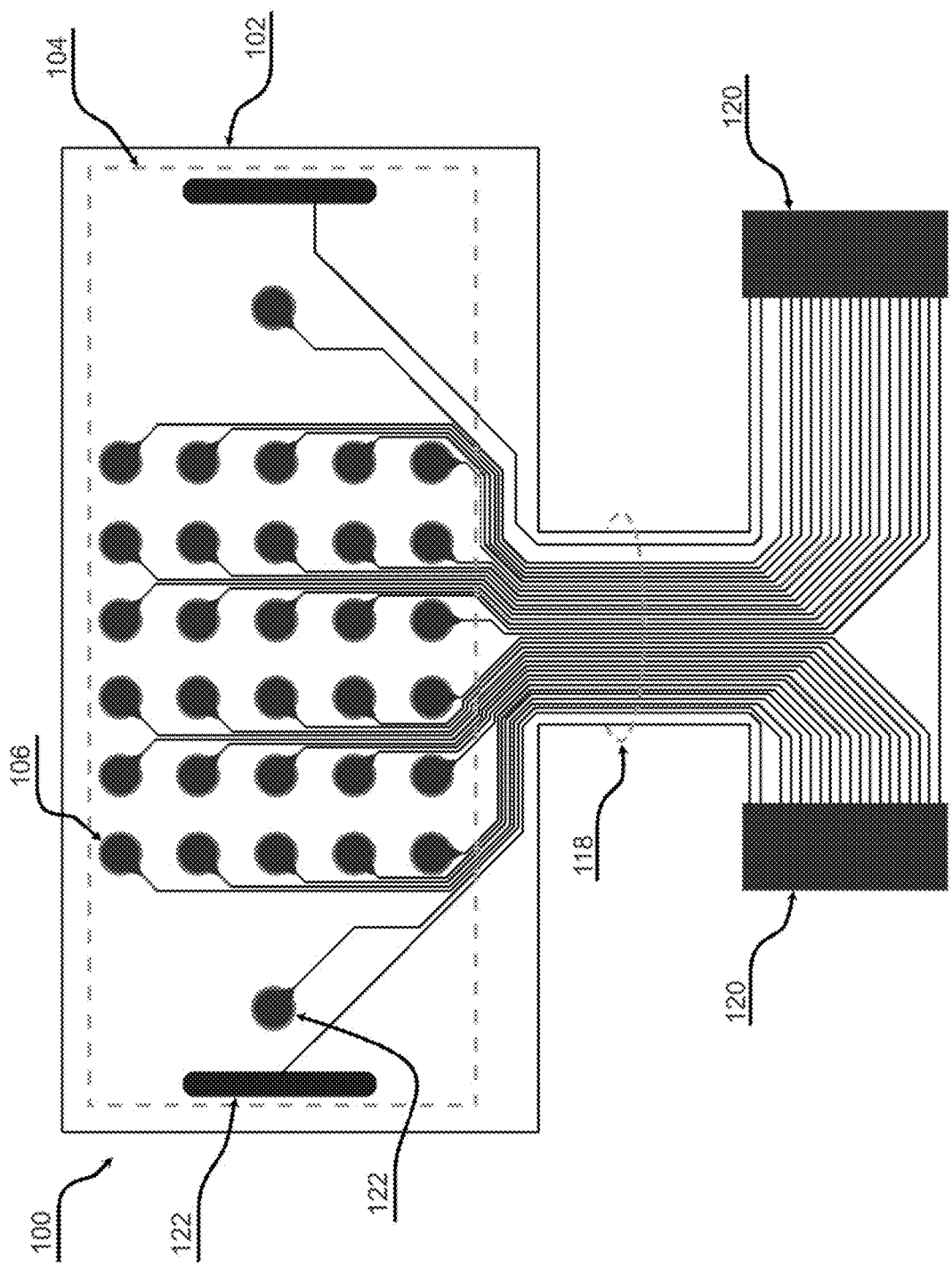
FIG. 2 illustrates another example electrode patch according to implementations described herein.
Figure 4:
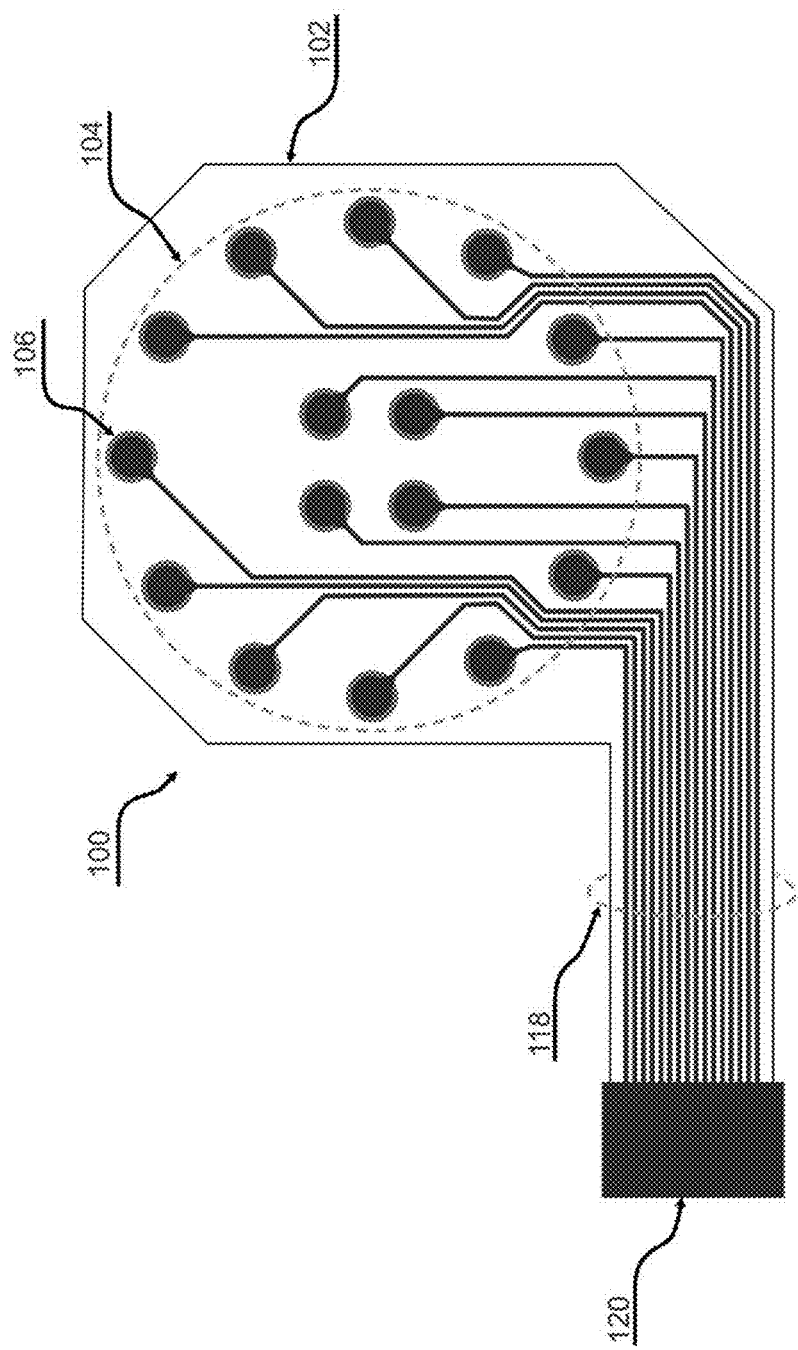
FIG. 4 illustrates another example electrode patch according to implementations described herein.
Figure 6:
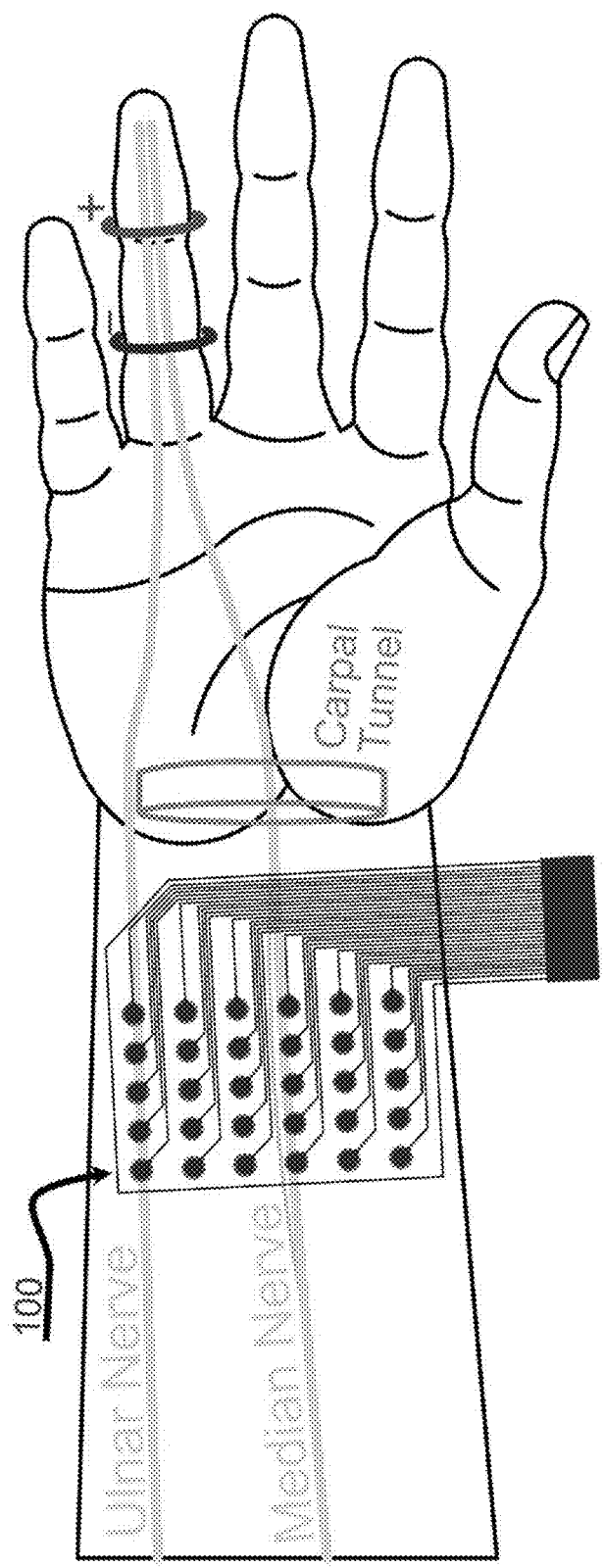
FIG. 6 illustrates an electrode patch applied to a patient's lower arm according to implementations described herein.

The electrode patch described herein such as those shown in FIGS. 1, 2, 4, and 6, for example, include more than two electrodes 106. Additionally, the electrodes 106 can be independently addressable. For example, the electrode patch 100 further includes a plurality of traces 118, where each of the traces extends between a respective electrode and a peripheral region 120 of the electrode patch 100. This is shown in FIGS. 1, 2, and 4. As described above, the traces 118 can be fabricated onto the flexible substrate 102. In some implementations, the traces 118 are optionally screen-printed onto the flexible substrate 102. In these implementations, the traces 118 are formed from conductive inks. Each of the traces 118 extends between one of the electrodes 106 (e.g., the electrode contact described above) and the peripheral region 120. Accordingly, an electronics module (described below) can be coupled to the electrode patch 100 at the peripheral region 120. The electronics module can be configured to apply stimulation and/or record electrical activity independently via each electrode 106. Additionally, the electrode patch 100 described herein is configured to operate (e.g., apply stimulus and/or record activity) more reliably and with higher resolution at the same anatomical structure (e.g. targeting the median nerve in a patient's wrist, as shown in FIG. 6). To target the same anatomical structure, in some implementations, center-to-center spacing between electrodes may be less than about 1 centimeter (cm). In other implementations, center-to-center spacing between electrodes may be less than about 0.5 cm. Additionally, the diameter of electrodes may be between about 1 centimeter and about several millimeters (e.g., 2-3 mm). Alternatively or additionally, in some implementations, as shown in FIG. 2, the electrode array 104 includes one or more reference electrodes 122 (or ground electrode, driving electrode, etc.). In other implementations, reference, ground, and/or driving electrodes are provided on separate patches. It should be understood that the number and/or arrangement of electrodes 106 shown in the figures are provided only as examples.

Figure 5:
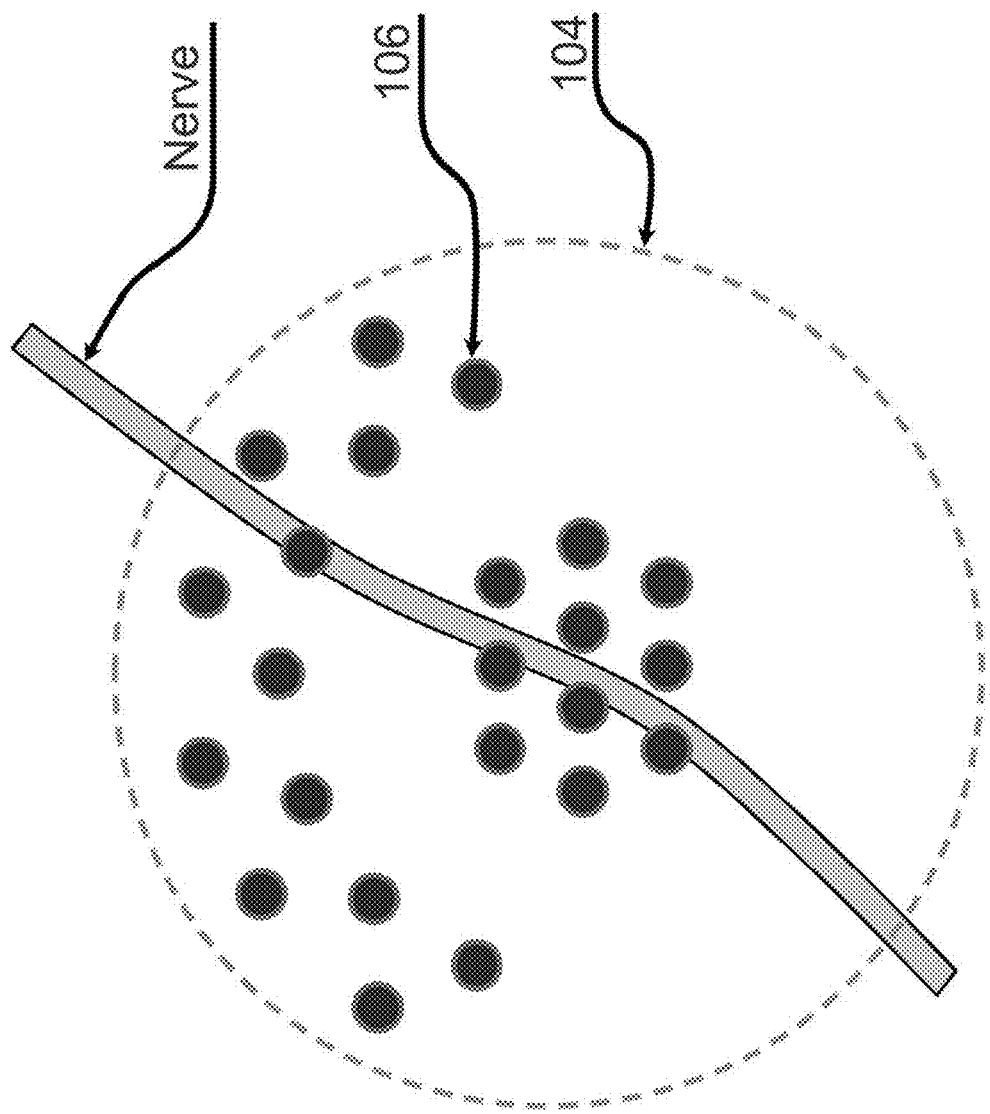
FIG. 5 illustrates the arrangement of electrodes in an electrode array according to implementations described herein.

In some implementations, the plurality of electrodes 106 are arranged in a grid. For example, the grid has a square, rectangular, or hexagonal shape. In other implementations, the plurality of electrodes 106 are arranged in a circle, semi-circular, or arc pattern. In yet other implementations, the plurality of electrodes 106 are unevenly distributed. FIGS. 1 and 2 illustrate the electrode array 104 with electrodes 106 arranged in a rectangular grid. FIG. 4 illustrates the electrode array 104 with electrodes 106 arranged a square grid (e.g., four central electrodes) and a circular pattern (e.g., twelve electrodes arranged around the four central electrodes). FIG. 5 illustrates an electrode arrangement with electrodes 106 arranged in a hexagonal staggered pattern (e.g., bottom group of electrodes) and a circular staggered pattern (e.g., top group of electrodes). This disclosure contemplates providing electrode patches with different numbers and/or arrangements of electrodes.

In some implementations, the electrode array 104 includes a first group of electrodes and a second group of electrodes. As described herein, the electrodes 106 are individually addressable. The electrodes 106 can be grouped by arrangement on the electrode patch 100 and/or by function (e.g., cathode/anode, stimulation/record, etc.). Optionally, the arrangement of the first group of electrodes is the same as the arrangement of the second group of electrodes (e.g., two spaced apart rectangular grids). Optionally, the arrangement of the first group of electrodes is different than the arrangement of the second group of electrodes. FIGS. 4 and 5 are examples. In FIG. 4, the first group of electrodes is arranged in a square grid (e.g., four central electrodes) and the second group of electrodes is arranged in a circular pattern (e.g., twelve electrodes arranged around the four central electrodes). In FIG. 5, the first group of electrodes is arranged in a hexagonal staggered pattern (e.g., bottom group of electrodes) and the second group of electrodes is arranged in a circular staggered pattern (e.g., top group of electrodes). Optionally, the first and second groups of electrodes are configured for different functionality. FIG. 5 is an example, where the first group of electrodes (e.g., hexagonal staggered pattern/bottom group of electrodes) is configured as an anode and the second group of electrodes (e.g., circular staggered pattern/top group of electrodes) is configured as a cathode. In other implementations, the first group of electrodes is optionally configured for stimulation and the second group of electrodes is optionally configured for recording. It should be understood that two electrode groups are provided only as an example. This disclosure contemplates grouping electrodes (by arrangement and/or functionality) into more than two groups.

Referring now to FIGS. 8-9B, the electrode patch 100 further includes a compression pad 114, which is configured to apply pressure to the electrode array 104. The compression pad 114 can be configured to wrap around a portion of the patient's anatomy. It should be understood that the size and/or shape of the compression pad 114 is provided only as an example. As shown in FIGS. 8 and 9A, the compression pad 114 includes a rigid member 116, where the rigid member 116 is configured to focus the pressure onto the electrode array. The rigid member 116 is optionally configured to focus the pressure onto a portion of the electrode array and/or onto one or more electrodes of the electrode array. As shown in FIG. 9A, the rigid member 116 applies pressure to the electrode 106, and the electrode is pressed further into the patient's skin. This is in contrast to FIG. 9B, where the electrode patch 100 does not include a compression pad. Additionally, the compression pad 114 includes at least one groove 126. Grooves 126 act as relief cuts, increasing flexibility or conformability of the compression pad 114. It should be understood that the number, size, shape, and/or arrangement of the rigid members 116 and/or grooves 126 are provided only as an examples. Alternatively or additionally, this disclosure contemplates providing one or more cutouts (e.g., similar to those provided in the flexible substrate and/or intermediate layer as shown in FIGS. 7A and 7B) in the compression pad 114. Cutouts act as relief cuts, increasing flexibility or conformability of the electrode patch 100 and also facilitate visibility of the underlying anatomical structure during placement of the electrode patch 100.

Figure 11:
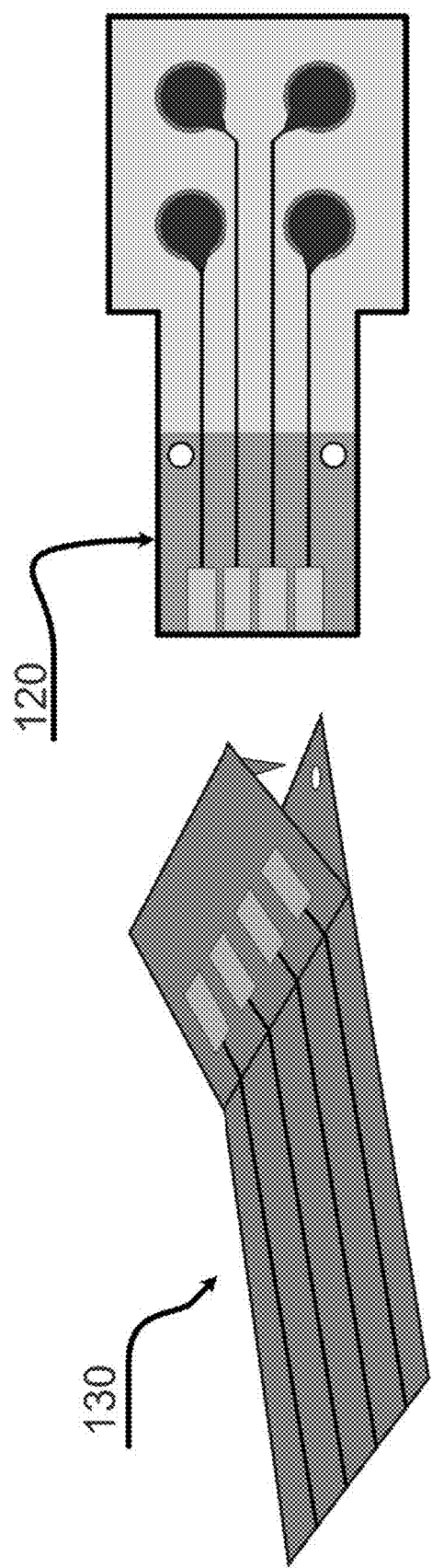
FIG. 11 illustrates a snapping connector according to implementations described herein.
Figure 12:
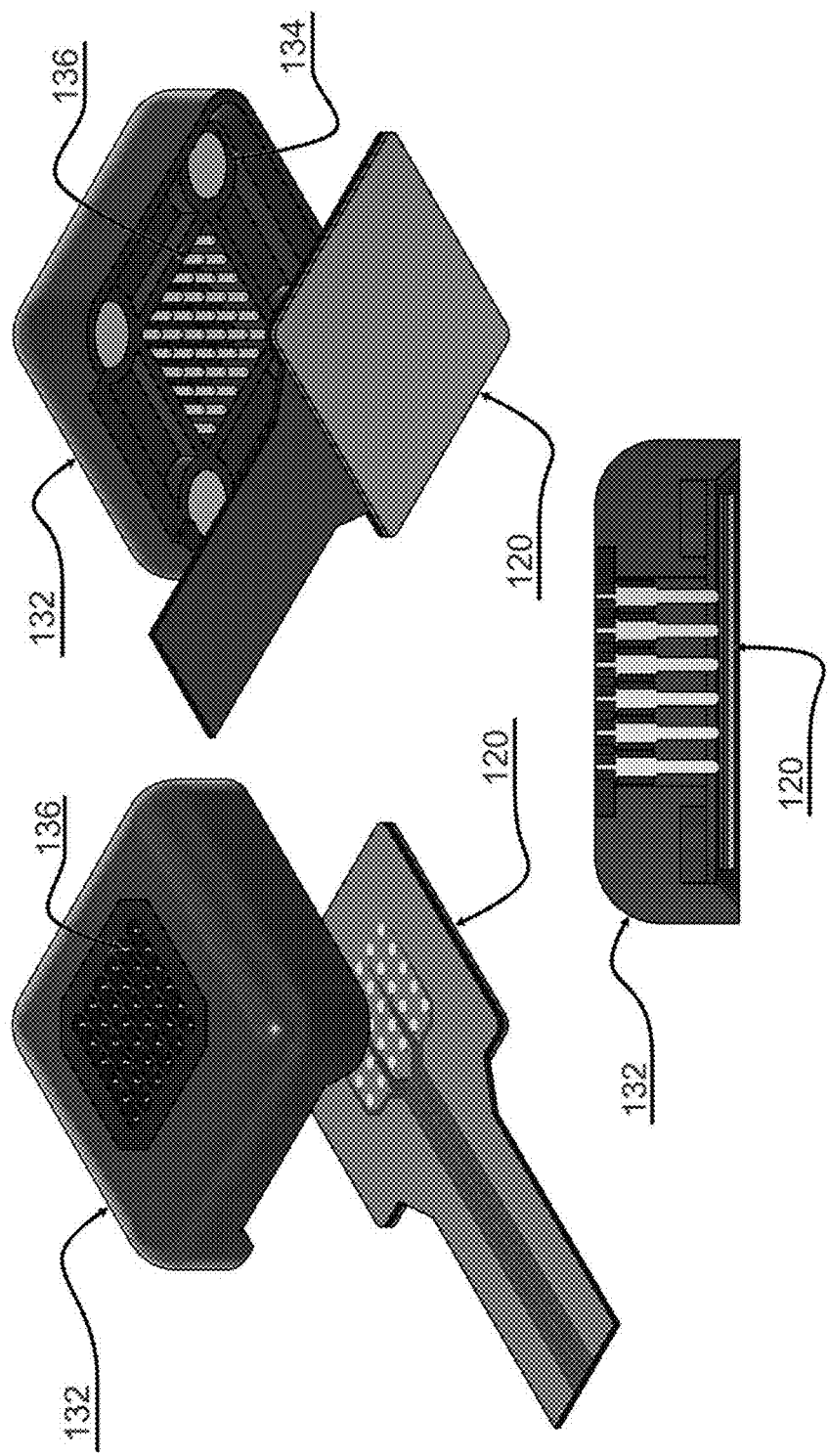
FIG. 12 illustrates a magnetic connector according to implementations described herein.
Figure 13:
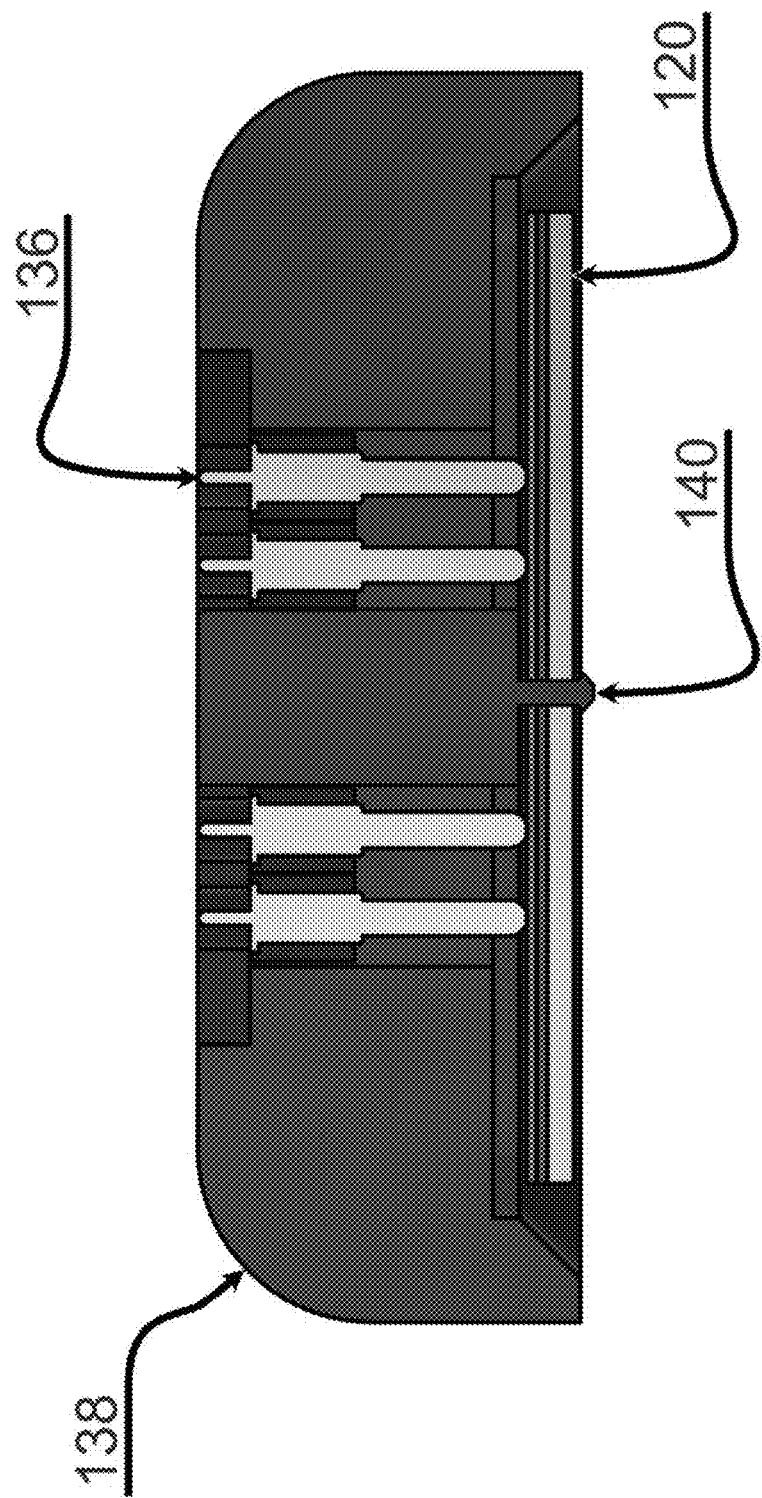
FIG. 13 illustrates a magnetic connector with locking mechanism according to implementations described herein.

Referring now to FIGS. 11-13, connectors for use with the electrode patches described above are shown. The connectors can be used to operably couple the electrode patch to the electronics module (described below). These connectors provide for both mechanical and electrical coupling. FIG. 11 illustrates a snapping connector 130 that aligns with the peripheral region 120 of the electrode patch. Compressible substrates or spring pins can be used to form stable connection between the connector 130 and the electrode patch. FIG. 12 illustrates a magnetic connector 132 that aligns with the peripheral region 120 of the electrode patch. One or more magnets 134 are used to mechanically couple the connector 132 and the electrode patch. Pins 136 provide electrical connection to contact pads at the peripheral region 120 of the electrode patch. FIG. 13 illustrates another connector 138 that aligns with the peripheral region 120 of the electrode patch. Pins 136 provide electrical connection to contact pads at the peripheral region 120 of the electrode patch. The connector 138 includes a locking mechanism 140 such as a button snap. The locking mechanism 140 secures and/or applies pressure between the connector 138 and the electrode patch for better mechanical and/or electrical coupling. The locking mechanism can also provide gross and/or fine alignment during the connector mating. In some implementations, the locking mechanism 140 is an alternative to the magnetic connector of FIG. 12. In other implementations, the connector 138 can optionally include one or more magnets for aligning the contact pads at the peripheral region 120 of the electrode patch.

Figure 14A:
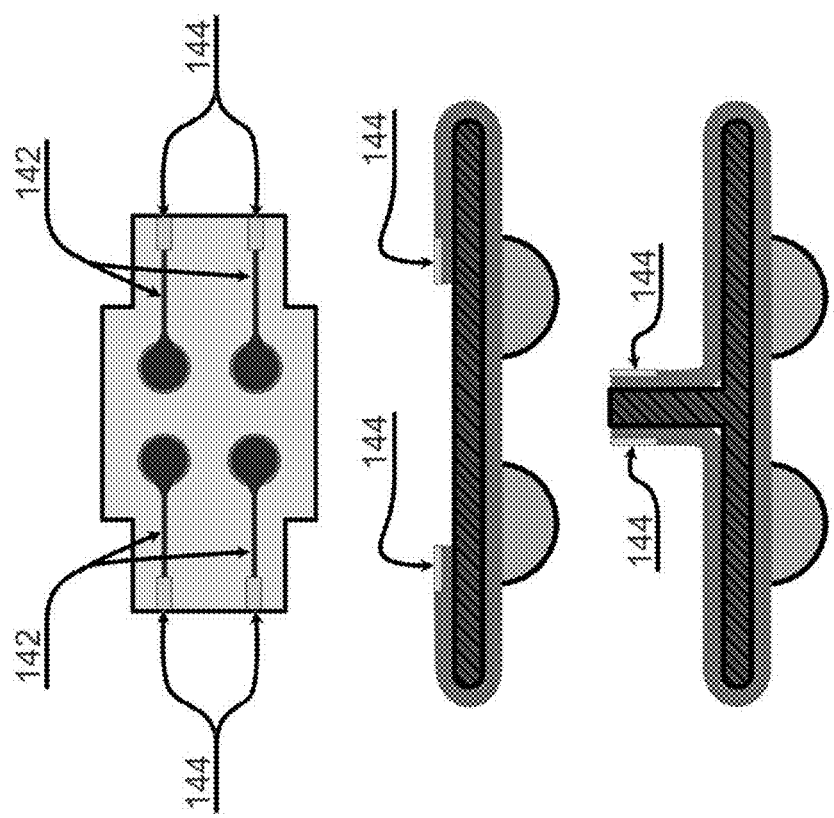
FIGS. 14A and 14B illustrate electrode patches with wrap around traces.
Figure 14B:
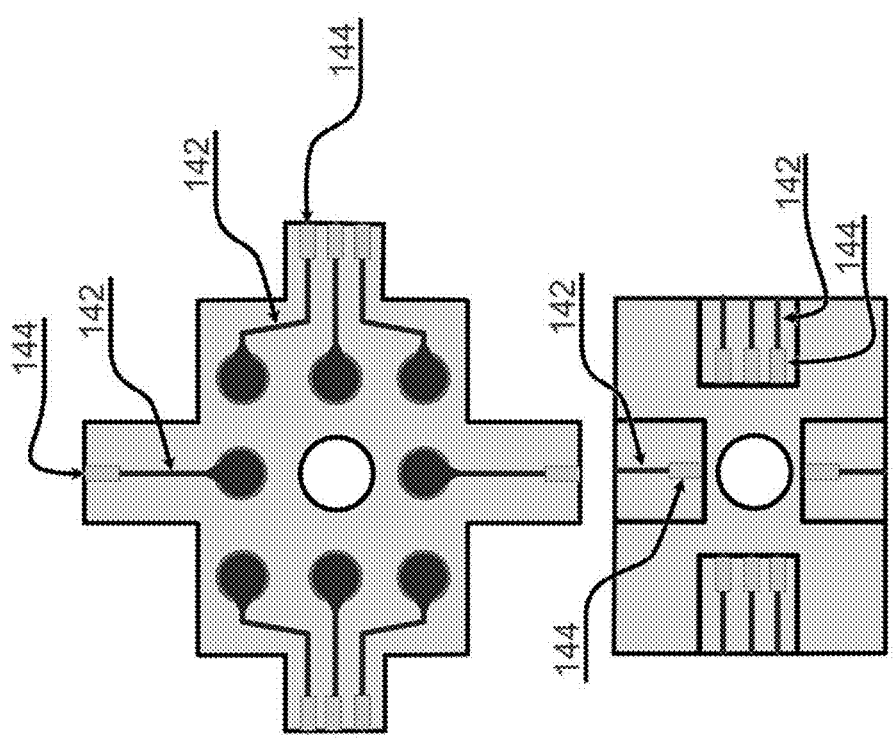

FIGS. 14A and 14B illustrate electrode patches with wrap around traces. In FIGS. 14A and 14B, the traces 142 and contact pads 144 are printed on extended portions of the flexible substrate. It should be understood that the contact pads 144 are located at the peripheral region of the flexible substrate (e.g., peripheral region 120 shown in FIGS. 1, 2, and 4). The extended portions are wrapped around another substrate (FIG. 14A) or simply folded over (without extra substrate) (FIG. 14B) such that the contact pads 144 are arranged on an opposite surface of the flexible substrate. In this way, the electrode patch can be manufactured without vias or through holes providing electrical connection between opposite surfaces of the flexible substrate.

An example system is also described herein. The system includes an electrode patch configured to interface with a subject's skin. This disclosure contemplates that the electrode patch can optionally be any one of the electrode patches of FIGS. 1-4, 6-7B, 9A, or 9B. The system also includes an electronics module 150 operably coupled to an electrode array of the electrode patch. The electronics module 150 can include stimulating electronics for stimulating nerves and/or recording electronics such as filters, amplifiers, and/or analog-to-digital converters. In some implementations, the electronics module 150 can include a power source such as a battery (e.g., a rechargeable battery). This disclosure contemplates that the electronics module 150 and the electrode patch can be coupled through one or more communication links. This disclosure contemplates that the communication links are any suitable communication link. For example, a communication link may be implemented by any medium that facilitates data exchange between the electronics module 150 and the electrode patch including, but not limited to, wired, wireless and optical links. In some implementations, the electronics module can be a computing device (e.g., computing device 200 of FIG. 15). Optionally, the electronics module 150 and the electrode patch can be coupled using one of the connectors of FIGS. 11-13.

The electronics module 150 is configured to deliver a stimulus to an electroactive tissue via the electrode array, or record an evoked electrical response from the electroactive tissue via the electrode array. The electroactive tissue can be a nerve. Although nerve tissue is provided as an example, this disclosure contemplates that the electroactive tissue can be tissue other than nerve tissue. Optionally, the electronics module 150 is configured to both deliver the stimulus to the electroactive tissue via the electrode array and record the evoked electrical response from the electroactive tissue via the electrode array. As described herein, the electrodes of the electrode array are individually controllable. In other words, the electronics module 150 is further configured to independently address each of the plurality of electrodes. In some implementations, the electronics module 150 is further configured to use the recorded evoked electrical response to adjust the stimulus delivered to the electroactive tissue In some implementations, the electronics module 150 is further configured to deliver a plurality of successive stimuli to the electroactive tissue via the electrode array with precise timing. For example, the plurality of successive stimuli are delivered precisely in phase or out of phase with other signals.

In some implementations, the electronics module 150 is further configured to cancel noise by averaging the plurality of successive stimuli. For example, the plurality of successive stimuli is two stimuli.

Figure 10A:
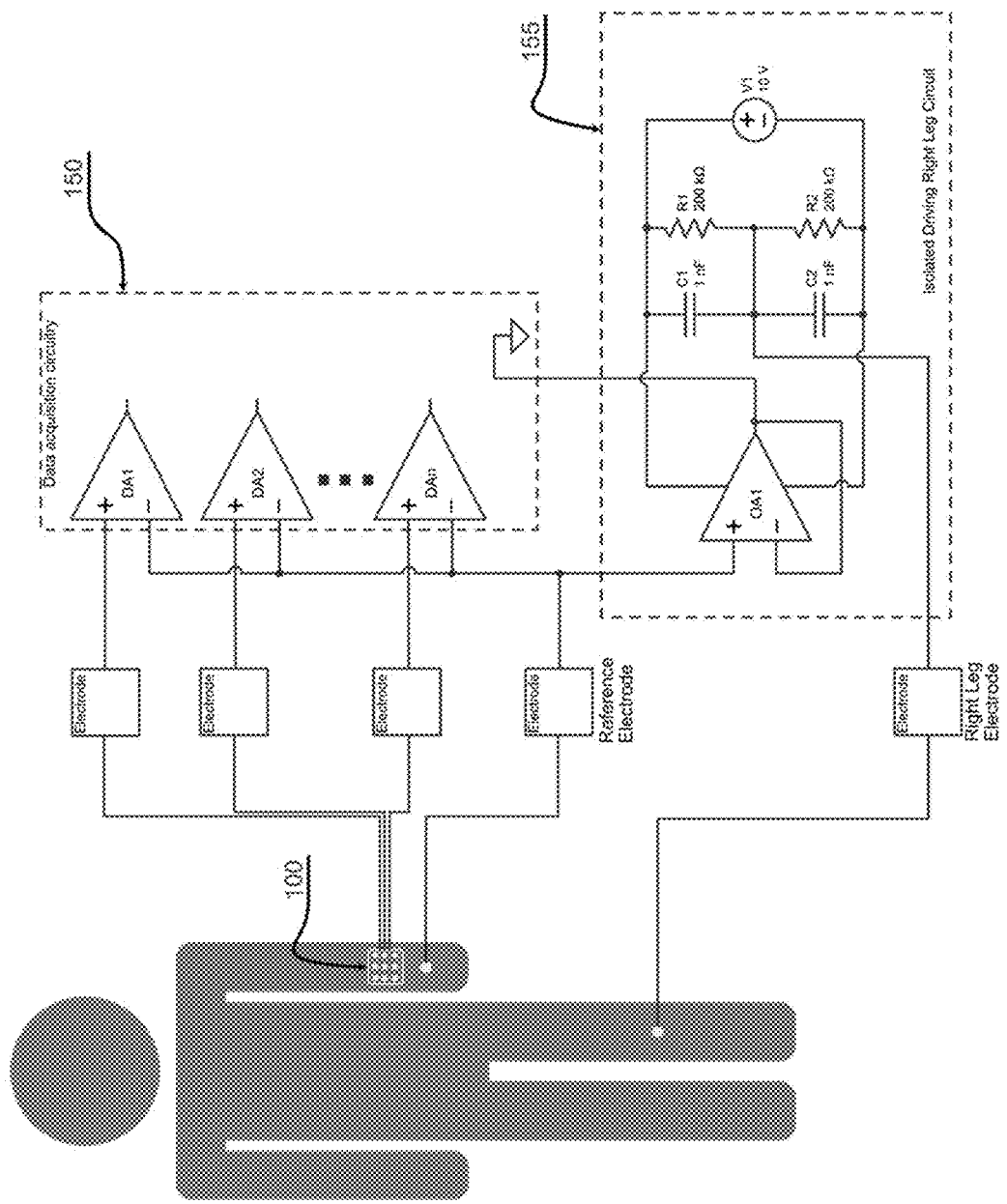
FIG. 10A illustrates an electrode patch operably connected to an electronics module according to implementations described herein.
Figure 10B:
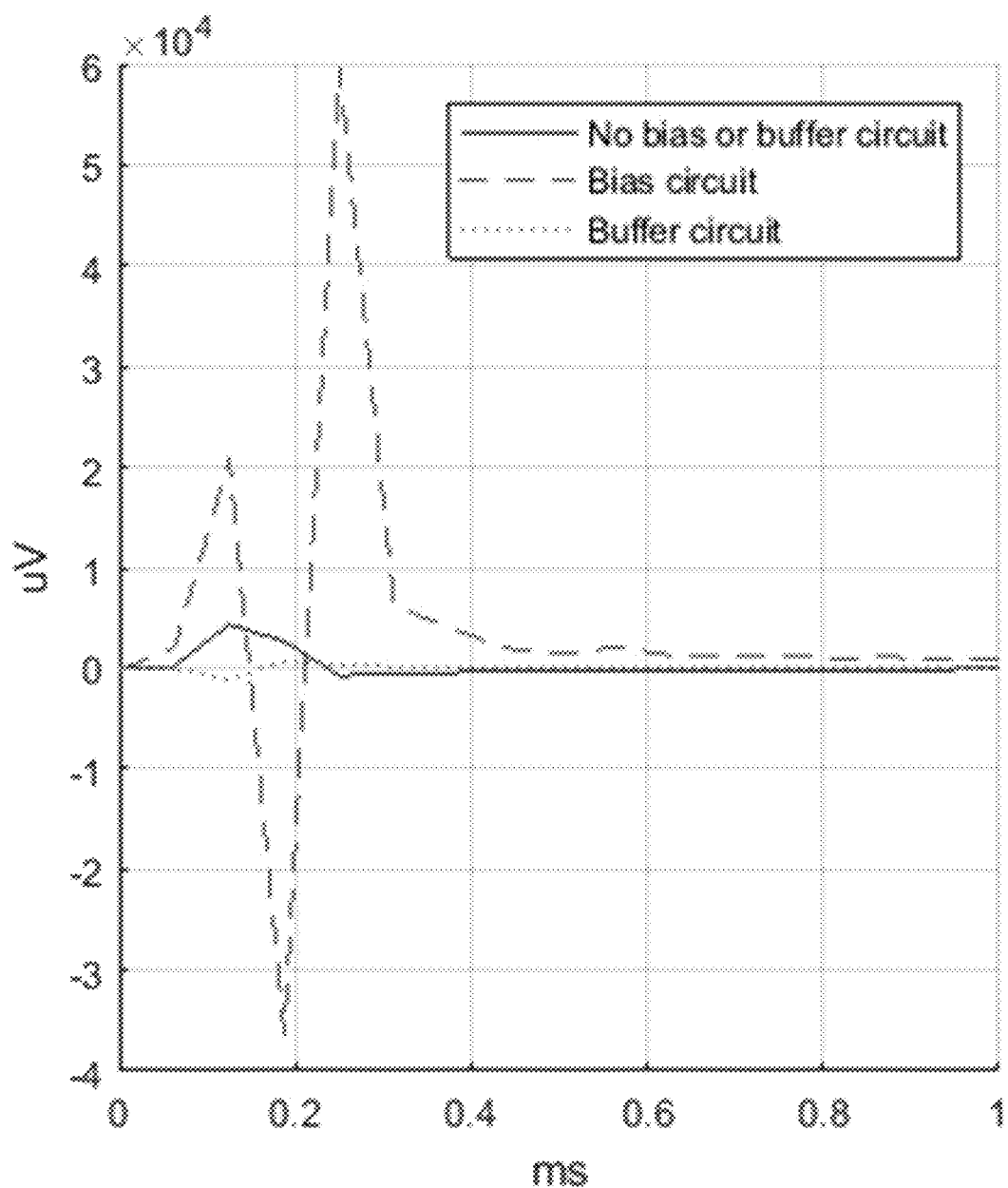
FIG. 10B is a graph illustrating the significant reduction in observed stimulation artifact achieved using the electronics unit of FIG. 10A, which includes a driven right leg circuit.

In some implementations, as shown in FIG. 10A, the electronics module 150 includes a driven right leg circuit 155. The driven right leg circuit 155 is used to mitigate stimulation artifact. As described herein, the driven right leg circuit 155 uses a feed-forward based circuit design to increase bandwidth. The driven right leg circuit 155 is configured to measure the subject's common-mode, and force a ground of the electronics module 150 to the subject's common-mode. FIG. 10B illustrates the significant reduction in observed stimulation artifact achieved using the driven right leg circuit 155.

Figure 16A:
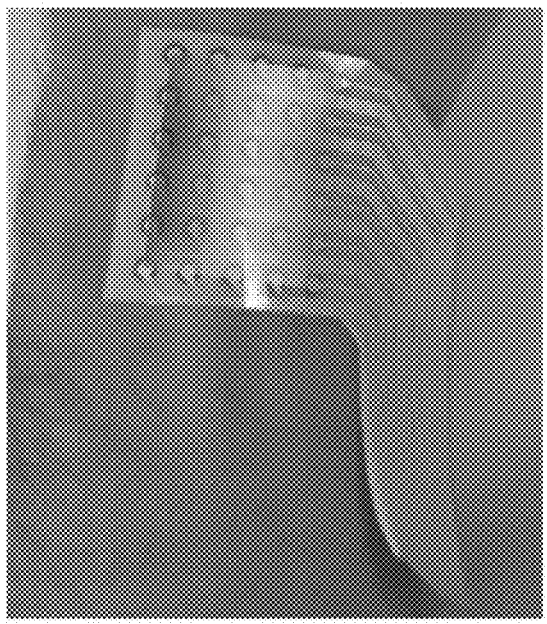
FIGS. 16A and 16B illustrate example applications for the electrode patches described herein.
Figure 16A:
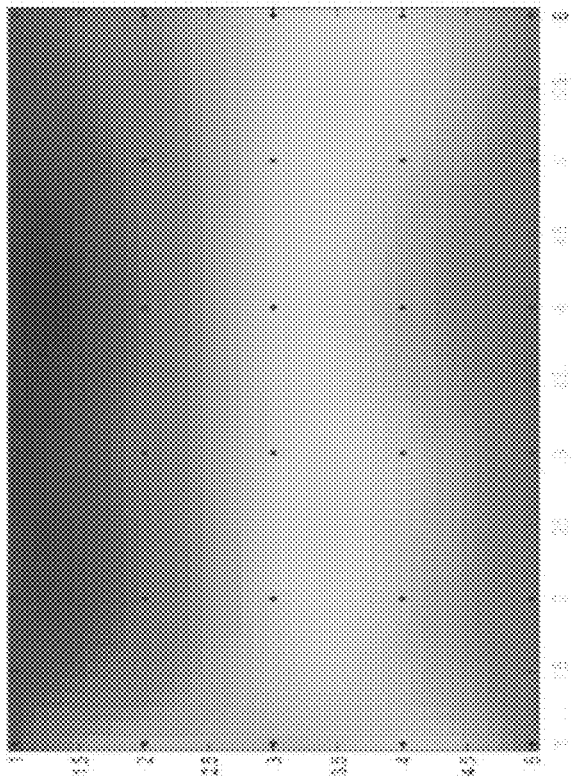

In some implementations, the electronics module 150 is further configured for functional nerve imaging. FIG. 16A. illustrates spatial activity mapping. For example, the electronics unit 150 is configured to automatically manipulate and monitor nerves, and the electronics unit 150 can be configured to identify the electrodes in the electrode array that acquire signals with the highest amplitudes. The results can be displayed as a heat map.

Figure 16B:
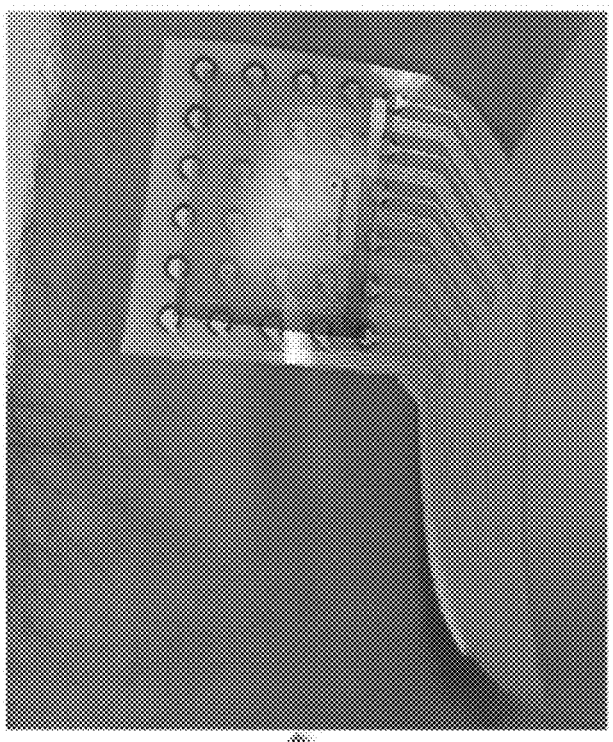
Figure 16B:
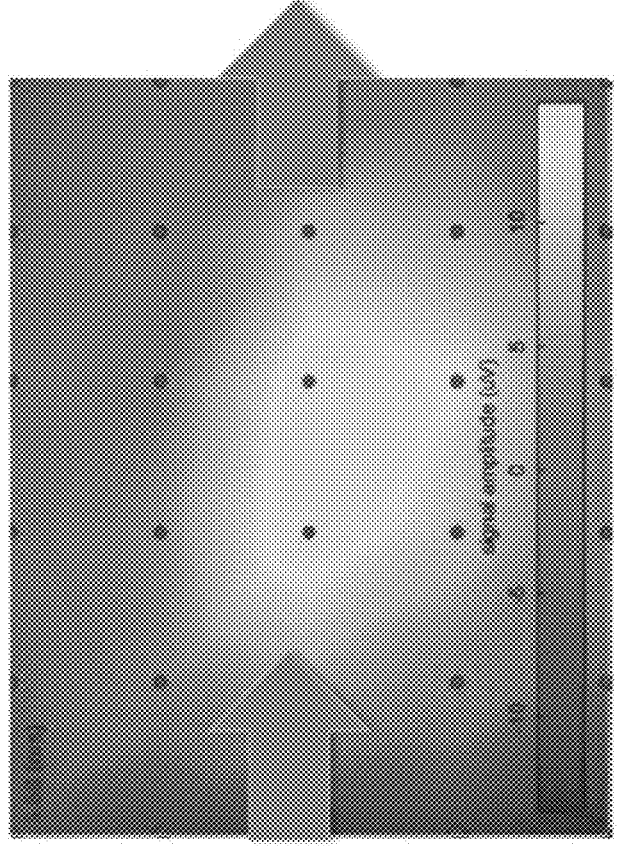

In some implementations, the electronics module 150 is further configured for a nerve conduction study. FIG. 16B is a still frame of signal propagation through the patient's median nerve, displayed as an animation or video. Different electrodes in the electrode array acquire the signal as it propagates along the nerve.

It should be appreciated that the logical operations described herein with respect to the various figures may be implemented (1) as a sequence of computer implemented acts or program modules (i.e., software) running on a computing device (e.g., the computing device described in FIG. 15), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 15:
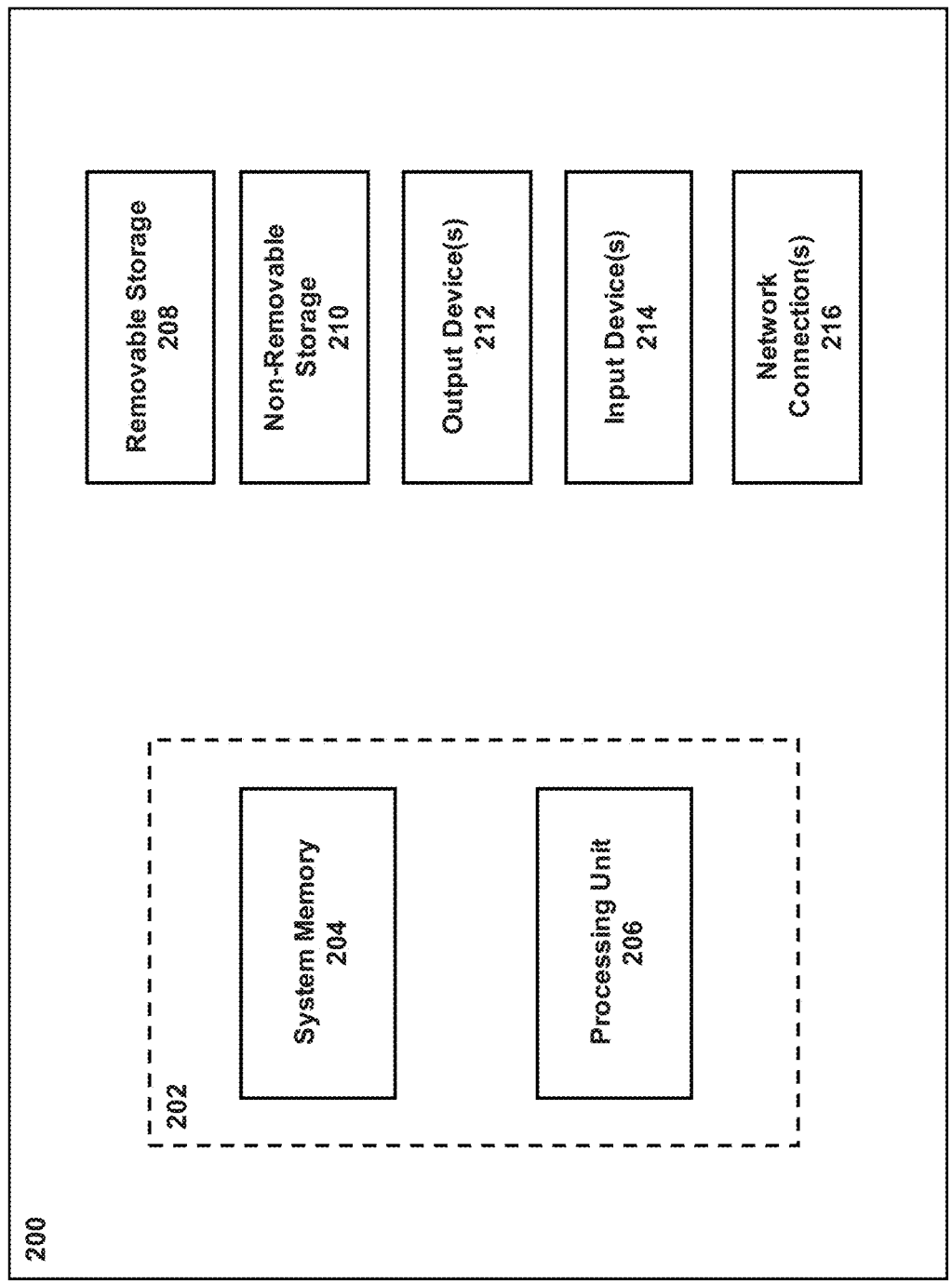
FIG. 15 is an example computing device.

Referring to FIG. 15, an example computing device 200 upon which the methods described herein may be implemented is illustrated. It should be understood that the example computing device 200 is only one example of a suitable computing environment upon which the methods described herein may be implemented. Optionally, the computing device 200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 200 typically includes at least one processing unit 206 and system memory 204. Depending on the exact configuration and type of computing device, system memory 204 may be volatile (such as random access memory (RAM)), non-volatile (such as read-only memory (ROM), flash memory, etc.), or some combination of the two. This most basic configuration is illustrated in FIG. 15 by dashed line 202.

The processing unit 206 may be a standard programmable processor that performs arithmetic and logic operations necessary for operation of the computing device 200. The computing device 200 may also include a bus or other communication mechanism for communicating information among various components of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 206 for execution. Example tangible, computer-readable media may include, but is not limited to, volatile media, non-volatile media, removable media and non-removable media implemented in any method or technology for storage of information such as computer readable instructions, data structures, program modules or other data. System memory 204, removable storage 208, and non-removable storage 210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

In an implementation described herein, the electrode-based system capable of interfacing with biological tissues can include an electrode patch connected to external electronics such as an electronic stimulating device, a biological signal amplifier, a computational device, and a user interface. The electrode patch includes a flexible substrate having a plurality of electrodes disposed thereon, the electrodes and system specialized for stimulating or recording from biological tissues, especially nerves.

Implementations described herein provide for electrode patches comprising a substrate, and at least one electrode set. In some aspects, the substrate is flexible and can have a surface, a periphery, and an electrode disposed on the surface, having a conductive trace extending from the electrode to the periphery of the substrate. In some aspects, at least one electrode array can be formed from a conductive substrate.

Implementations described herein also provide for an electrode system comprising an electrode patch, an external electronics assembly connected to the electrical contact of each of the plurality of electrodes, wherein the external electronics can be adapted to at least one of stimulate and/or measure electrical activity from each electrode. It is further contemplated that each of the electrodes can be individually addressable and that, in operation, the electrodes are adapted to be selectively functionally integrated via the external electronics assembly. Existing Issues of practical implementation and low resolution recordings can be resolved through electrode array-based techniques. A recording array enables higher spatial resolution, including information on directionality of impulses and location of nerve, and allows for a higher margin of operator error regarding anatomical placement of the electrodes. An array also provides signal redundancy, which can provide higher data fidelity and allow researchers to determine propagation properties of specific impulses, an impractical feature using traditional large bipolar electrodes. On the stimulation side, an electrode array similarly allows for a higher margin of error in electrode placement, while increasing capabilities for precisely controlling current delivery to target tissues for increased selectivity.

While conventional systems and methods capture a signal differential measurement, the electrode array described herein creates a "functional imaging" platform, allowing clinicians to accurately monitor disease progression (e.g. progression of diabetic peripheral neuropathy) or therapeutic responses (e.g., quantifying axon growth after nerve regeneration surgery). At the same time, the electrode patches described herein can fundamentally remove the guesswork of electrode placement due to anatomical variations. In addition to improved performance, the capacity of the system for automation can reduce the time required performing the experiment, because the electrode patch eliminates the need to "hunt-and-peck" for nerves. As a result, the electrode patches described provide an improved, cost-effective tool to diagnose disease and manage health.

Implementations described herein further provide for methods for using an electrode system comprising the steps of providing an electrode system, applying the electrode patch to a target region comprising at least one electroactive tissue such as a nerve, selectively stimulating a first portion of the plurality of electrodes, and/or selectively recording the evoked electrical activity from a second portion of the plurality of electrodes. In some implementations, electrodes can be distributed in different regions of the same patch or divided between multiple patches. Specialized connectors for interfacing the electrode patch with external electronics are described, as well as electronics configurations for minimizing noise and stimulation artifact and conditioning recorded signals. Electronics and software configurations are described for processing and analyzing measured signals and optionally providing feedback for adjustment of the stimulation.

Stimulation Artifact and Noise in Biological Recordings

Conventional nerve conduction studies have typically been limited by the presence of stimulation artifacts that obscure evoked nerve and muscle signals. The recording of evoked nerve signals has to take into account many issues, including 1) the magnitude of the signals themselves, which is on the order of a few microvolts, and 2) the magnitude of the stimulation artifact, which can be on the order of several volts. The small magnitude of the signals requires the use of very-low-noise circuitry. Electrode noise can be proportional to electrode size and impedance and there are resulting constraints on the minimum size of electrodes that can be practically used. The stimulation artifact, a result of the high voltages required to elicit a response through the skin, is in turn a direct consequence of the induced electric field from the stimulation leads and circuitry, the potentials (differential and common mode) induced in the body, the accumulated charge in the electrode interface, and of the effect that these induced voltages have on the signal-chain filters and other elements after stimulation. The problem is one of relative scales: stimulation signals are on the order of volts, while recorded signals are on the order of microvolts. These mismatches generate artifacts that saturate the signal acquisition chain, which has to recover fast enough to be able to measure the signals of interest.

In practice, such stimulation artifacts can be minimized by increasing the distance between the stimulation and recording electrodes, allowing the stimulation artifact to dissipate before the evoked potential reaches the recording site. While effective, increasing the distance between the stimulation and recording electrodes is sometimes impractical, potentially reduces sensitivity, and also makes it difficult to assess peripheral nerves over comparably short lengths.

For example, a short region of conduction velocity slowing (e.g., the median nerve at the wrist, as in carpal tunnel syndrome) can be clearly seen when the stimulus and recording electrodes lie directly on either side of that region; however, if the electrodes are separated from that region by an extended length of healthy non-pathological nerve, the net observed conduction velocity can be within the accepted clinical range despite a disease state. Accordingly, ideal stimulating and recording electrodes should incorporate a mechanism for preventing, removing, or reducing stimulation artifact, allowing stimulation and recording to occur in close proximity to each other and enabling a wider variety of focal nerve assessment.

The electrical ambient noise, which can reach tens of volts on a patient, has to be reduced via the use of (1) analog elements, such as differential recordings with high common-mode rejection and suppression, and (2) signal processing elements such as adequate filtering, undesired component extraction and removal, sub-microsecond synchronization of acquisition variables, trial averaging, out-of-phase interference cancellation, and other similar techniques.

In addition to the actual common-mode voltage present in a patient, the acquisition system has to take into account the unavoidable skin-electrode impedance and environment mismatches that reduce amplifier performance. This leads to requiring a ratio of signal to common-mode interference (CMRR) which can exceed 120 dB in many applications. Although amplifiers specifically designed for this purpose can reach 100 dB of CMRR, this performance will be somewhat degraded due to electrode and signal path mismatches. This means that additional circuitry has to be introduced in order to further improve the overall CMRR.

The traditional design that has been used for this purpose is known as a Driven Right Leg (DRL) circuit design. In a typical DRL circuit, an additional electrode is introduced, known as the DRL electrode. A feedback amplifier is used to measure the common-mode of the patient (normally extracted from a node inside the differential amplification circuitry) and apply a cancelling signal through an additional electrode, in order to force the measured common-mode to the desired reference (allowable patient current-leakage restrictions thus come into play).

Guermandi et al., "A DgRL for Improved Common Mode Rejection in Bio-Potential Acquisition Systems" describes a recent modification for EEG applications, termed the "Driving Right Leg" (DgRL) circuit. DgRL is a feed-forward design that considerably improves performance. Instead of forcing the patient common-mode to the desired value, this design measures the patient common-mode and forces the isolated data acquisition system ground to that value. As the data acquisition system is kept at the same potential as the patient, the common-mode is considerably reduced. This technique can lead to a better than 70 dB improvement in CMRR, as this improvement is mostly given by the gain of the amplifier being used.

In the systems described herein, the principles of Guermandi's DgRL design are applied to a new application with different constraints compared to the original EEG application. In the application of peripheral nerve stimulation and simultaneous measurement of evoked activity, the challenge of the stimulation artifact is introduced. Furthermore, the stimulation artifact can be particularly pronounced in cases where the stimulation and recording electrodes are close together, for example, when provided on the same electrode patch as described herein.

A traditional DRL circuit design performs poorly in the case of stimulation artifact because of its necessary bandwidth limitations imposed to maintain stability. The DRL circuit is a feedback circuit that involves several stages including unknown impedances, design limitations lead to a low-bandwidth operation (generally <200 Hz) and an overall improvement of CMRR of around 40 dB for the power-line interference. For applications described herein this bandwidth is a limitation, because (1) stimulation signals can introduce large high-frequency common-mode components that cause recording artifacts, and (2) the low-frequency pole will react to the fast stimulation components very likely making the artifact worse.

As noted above, principles of Guermandi's DgRL design have been applied to a new application (e.g., stimulation), and the circuitry is accordingly. Aside from the intended purpose of noise reduction, an increase in the possible bandwidth provided by the feed-forward based circuit design is exploited. With a properly selected amplifier, it has been found that this circuit design can operate with bandwidth in excess of 10 MHz, and it has been further demonstrated that this bandwidth is able to cover the frequencies introduced by our stimulation artifact. Thus, not only does the design based on DgRL principles (see FIG. 10A) result in an improvement in CMRR, but it is able to operate in the presence of stimulation artifact. Furthermore, it has been shown shown that it can significantly reduce observed stimulation artifact (FIG. 10B). It has furthermore been recognized that, while not apparent from the schematic of FIG. 10A, this circuit injects current into the patient as with a traditional DRL circuit, but that the required current will be reduced as it is now shared with the current injected into the data acquisition equipment. Thus, the circuitry of FIG. 10A increases bandwidth, reduces the number of components, and remove noise performance requirements on the ground amplifier.

Once the signal has been acquired by the analog front-end, it has to be converted to the digital domain. Towards this end, technological advances have provided high-levels of precision, but other considerations must be considered: (1) Electrodes present different and varying potentials that slowly wander, causing problems even in differential recordings (DC-wandering); (2) sample acquisition has to be synchronized to the stimulation system to avoid losing information due to jitter across multiple stimuli; and (3) if mains, or other periodic or random interference that might arise from the stimulus equipment needs to be reduced via post-processing, sample acquisition should incorporate it.

To avoid the DC-wandering problem and to improve patient safety, AC-coupled analog stages are commonly used. However, given the wide dynamic range now made available by high-resolution ADCs, it has become possible to DC-couple the analog stage and post-process the signals to remove the DC-wandering components. This also reduces artifact problems, as it removes the slowest time-constant in the signal acquisition chain.

Given that the system is controlled by a digital infrastructure, stimulation can be triggered with the same time-base (system clock) used for data acquisition with minor additional design considerations. However, some systems (such as but not limited to implanted stimulators) might make this synchronization impossible, so these would have to be treated as external signals. Just like with other interfering signals that could become problematic, the addition of a means to sample these signals can be provided. Making them available for later post-processing.

In some cases, monitoring of nerve or muscle signals periodically over extended periods of time is valuable in monitoring progression or recovery from disease or injury. Making fine, quantitative assessments of nerve or muscle function can be difficult or impossible with existing low-resolution and manual techniques.

Measuring evoked potentials is limited by the current capabilities of conventional nerve conduction study equipment. These limitations include a lack of spatial resolution, repeatability, sensitivity, and practicality. High resolution, fine, sensitive, quantitative, and practically implemented assessments of nerve or muscle function would improve current diagnostic capabilities and help to inform optimal treatment. For example, in the surgical treatment of carpal tunnel syndrome, a range of surgical and non-surgical treatment methods are often used, ranging from braces, to physical therapy, to injections, to different types of surgery. More quantitative assessments of nerve function might allow neurologists to make better decisions for the appropriate therapy, whether it might be conservative treatment or a surgical intervention. For example, measures of local conduction velocities and signal amplitudes near and through the carpal tunnel might allow more advanced analysis and diagnosis with increased predictivity of an optimal treatment option. A more sensitive, higher resolution, more quantitative, and/or more practically administered assessment method would also allow earlier and more accurate evaluation of recovery following treatment intervention, to determine whether a follow-up procedure is necessary.

Invasive peripheral nerve studies have significantly increased our understanding of neurophysiology, nerve pathophysiology, nerve regeneration, and neuromuscular interactions. Unfortunately, capabilities to translate this knowledge into more broadly applicable, non-invasive procedures have not progressed significantly. Current non-invasive procedures require well-trained operators, who must contend with multiple limitations. As a result, electrodiagnostic procedures are often labor intensive for the operator, uncomfortable and/or painful for the patient, and imprecise in the measurements—leading to a reluctance to perform experiments and ambiguity in the results. These present-day limitations are the result of two significant problems: (1) lack of spatial resolution in recordings, and (2) lack of data fidelity for low-amplitude signals.

Advanced capabilities for interfacing with body tissues would be useful in many different application areas. Electrical stimulation, for example, is used for a variety of therapeutic purposes. Transcutaneous electrical nerve stimulation (TENS) and high frequency nerve stimulation are examples of electrical stimulation paradigms for reducing pain. Intra-operative neural monitoring (IONM) is used to reduce the risk of nerve damage to patients undergoing sensitive and invasive procedures involving the brain, nerves, and spinal cord. Through improved systems, IONM may be improved and used on nerves which are typically harder to record from but may be more clinically relevant.

Electrodes

Electrode patches including an electrode array are described above with regard to FIGS. 1-10B. In these implementations, the electrodes include conductive ink and hydrogel. In implementations described herein, electrodes may be composed of any substantially conductive material including but not limited to metals (such as gold, silver, silver/silver chloride, platinum, iridium, and various alloys or oxides, or conductive inks such as carbon or metallic ink), conductive polymers, gels, or hydrogels, or combination materials such as silver/silver chloride with an overlying gel or hydrogel. Electrodes can be designed for transparency, for example from indium-tin oxide or conductive materials of sufficient thinness or in a porous/mesh design to enable transparency. Hydrogels offer advantages of being soft, chemically tunable, biocompatible, and ionically conductive. Hydrogels can refer to polymeric materials capable of holding water within their polymer structure.

The electrodes can have various geometries, including two-dimensional (2D) and three-dimensional (3D) geometries. For example, the electrodes can be raised so as to press into the skin, or be raised and sharp with the intention of penetrating, indenting or compressing the skin. In one embodiment, individual electrode sites include hydrogels with a raised (for example, convex or dome-like) geometry that extends from the plane of the electrode. This raised geometry confers several advantages, including, but not limited to pressing into the skin for increased effective surface area, more intimate skin-to-electrode contact, better isolation of the electrode/skin interface to prevent shunt currents between electrode sites, and a reduction in distance between the electrode and underlying target tissue. In some embodiments, an intermediate material is placed between the substrate and the skin that can be flexible and or compressible, such as a foam, rubber, silicone. In certain embodiments, indentation of the skin from the raised/protruding electrodes can persist after removal of the electrodes, providing a precise marker of the relative location of each electrode with respect to patient anatomy and physical reference sites or "landmarks".

In another embodiment, the hydrogel is underfilled, for example relative to an intermediate substrate like foam or rubber. In this case, the skin can be push into the cavity adjacent to the electrode, and thereby enhancing the electrode skin interface by providing isolation and preventing shunt currents. Here, the intermediate material can be rubber or the interface configured such that there is or a negative pressure that keeps the skin drawn into the concave electrode.

In some embodiments, the electrode sites comprise one or more penetrating elements designed to penetrate the skin. For example, microneedle structures can penetrate the outer, high impedance layers of skin, such as the avascular stratum corneum without penetrating to deeper vascular layers, where nerve innervation is more abundant.

It is contemplated that descriptions of electrodes or arrays of electrodes might also apply towards other structures able to measure from or interact with tissue. For example, an electrode might be replaced by an light emitter such as a light emitting diode (LED) able to optically stimulate tissue, for example through natural or optogenetic techniques. Similarly a photodiode or infrared (IR) sensor may be used to measure an optical property of the underlying tissue. Chemical, acoustic, ultrasonic, magnetic, mechanical, radiofrequency (RF), and a variety of other modes may be similarly used to interact with the tissue. Any interaction might be defined as but not limited to monitoring, measuring, or stimulating tissue.

Electrode Layout

In some embodiments, multiple electrodes are arranged into one or more arrays able to independently stimulate or measure a plurality of distinct sites in the same region of tissue. As described herein, an array consists of a plurality of electrodes, and in some implementations, includes any ground, reference, or driving electrode. These arrays can be used to measure or stimulate multiple individual sites across an area of tissue. For example, placement of an array of electrodes allows broad but also dense coverage of tissue, so that imprecise placement, even with relatively little knowledge of patient anatomy, can still result in one or more individual electrodes being in the precise target location desired for stimulations or measurements. For measurements, a sufficiently dense array allows for high spatial resolution in recordings, for example to map the course of one or more underlying nerves or to map propagation across a muscle. For stimulations, a dense array can allow precise stimulation of a subset of a nerve or muscle. Independent selective stimulation at multiple electrodes in a spatiotemporally graded fashion can be used as a strategic delivery method to achieve the effect of "current steering," "charge steering," or "beam forming" for the focusing of stimulation to one or more precise target sites. This method can allow for targeting of regions from a 2D perspective on the skin or to result in current delivery at a deeper or more focused level of tissue. One or more electrodes at the opposite side of the target anatomy can be present to influence the path of the delivered current. A multitude of electrodes, in the same or separate patches, can be used to conform to the patient's anatomy or wrap around in a loop to effectively adapt current delivery in a more 3-dimensional manner. Known techniques of "temporal interference" can be used or adapted to an advantageous array-based format to better achieve targeted stimulation of underlying tissues.

Given the assumption that the current through the tissue follows the electric field lines generated by the cathode and anode, the path of the current can further be modified by altering the electric field characteristics. While the cathode and anode inject and receive a direct current (DC) current, tertiary electrodes may push or pull the electric field towards strategically positioned locations across the tissue. These tertiary electrodes are not designed to receive or inject any current, and thus, they may be implemented with a conductive core surrounded by a nonconductive shell which interfaces with the skin. The voltage applied to these electric field modifying electrodes can be varied in amplitude or polarity to effectively pull or push the electric field to effectively control the depth at which the current passes through the tissue.

Electrodes can be arrayed in a hexagonal layout or similar patterns to increase the electrode density. The layout of the electrode array can be chosen based on the electrode shape (e.g. a hexagonal layout with hexagonal shaped electrodes), for example to increase density.

In some cases, it is desirable to apply pressure on the electrode to increase the electrode-skin contact, move the electrode closer to the underlying target tissue, reduce superficial shunt currents, or conform the tissue to the electrode (e.g., pressing the skin into a concave electrode). A wrap or band can be provided to apply this pressure. The wrap or band may include the compression pad of FIGS. 8 and 9A. In some cases the wrap or band can incorporate a rigid member (e.g. flat, curved, or otherwise shaped to fit the underlying anatomy) overlying the electrode array designed to selectively apply pressure on the electrode array pushing it into the skin. In further cases, the wrap can have several rigid structures such as protruding elements, strategically designed to focus pressure on one or more locations on the electrode array. For example, rigid members can overlay each electrode, such that pressure is optimally applied just at the electrode sites. In one embodiment a solid member has grooves or thinned out sections such that it is flexible but still rigid at the electrode sites. The intent is the apply pressure only where it is needed to improve the electrode to skin contact, but also to provide a consistent spacing between electrodes while maintaining flexibility. In other embodiments, pressure can instead be applied around or between the electrodes, to minimize shunt currents for example. In this case, there can be a pattern of holes coincident with the electrodes in the patch. To ensure proper alignment, a mechanical interface can be integrated such as alignment guides. In some instances, the compression pad can be permanently fixed as an additional substrate of the patch or entirely removable as a separate entity to be used for multiple sessions.

Similarly, stimulation can be strategically delivered to minimize the associated stimulus artifact as measured from one or more recording electrode sites. For example, several unique stimulation patterns can have the same stimulation effect on the underlying nerve or muscle, but result in different isopotential lines across the body. Electrode patterns in conjunction with strategic stimulation can result in isopotential field lines which coincide with the recording electrodes at varying angles, eliminating or reducing contributing components of the measured stimulus artifact. In some cases, consecutive stimuli can be delivered as the system automatically determines optimal stimulation patterns to achieve the desired effect on tissue and/or reduce stimulation artifact seen by measurement electrodes. These consecutive stimuli can use a lower current than the final stimulations to reduce the patient discomfort.

To achieve the desired effects, for example similar to those described above, the electrode array may not be arranged in an evenly spaced or regularly distributed spatial array pattern. Rather, electrodes can be patterned into layouts of various shapes and densities. For example, one portion of the array designed to overlie the target tissue and function as an effective cathode. A separate portion of the array can have a different spacing and be designed to function as an effective anode. This anode portion of the array can be distributed into one or more concentric circles or arcs surrounding the cathode portion of the array. This arrangement can allow manual, semi-automatic, or automatic selection of various individual (or multiple groups of) electrodes on the anode portion of the array, while holding the stimulation from the cathode portion of the array constant, in order to achieve the same stimulation effect, but reduce stimulus artifact. This arrangement allows fine tuning of the angle of electric field lines, such as to be maximally selective in current delivery to particular portions of target tissue, using a fixed number of electrodes. Adjacent electrodes can be stimulated together with fine-tuned percentages of current delivery through each for high precision tuning of current delivery to mimic an intermediate virtual electrode. Additionally, tuning of electric field lines can allow for minimization of the stimulus artifact, as it has been shown that recording with electrodes placed parallel to the stimulation field lines results in a minimized stimulus artifact. Another possible embodiment includes a singular adhesive cathode which functions as the articulation point of a mobile anodal metal electrode which can be positioned along any point is a circle or arc about the cathode. In any of these designs, the electrode size as measured by the shape and dimension of the hydrogel and electrode pad can differ even within the same patch.

In some configurations a solid sheet of hydrogel or other charge conducting material is provided between the electrode contact on the substrate and the skin, where the bulk resistivity of the material is high enough to discourage current spreading in the layer and maintaining selective recording or stimulation. (Keller, Kuhn, 2008). In other configurations regions of the material have varied resistivity. The resistivity of the layer might influence the optimal sizing and spacing of electrodes.

In some configurations, the phenomenon of "temporal interference" is used to target stimulation to deeper depths in the tissue.

Other array configurations can be designed to match particular features of the external anatomy or anatomy of underlying target tissues, such as elongated or branched nerves.

Electrode Array—Physical Design and Packaging

One or more electrodes can be integrated with a carrier or substrate. This substrate can be composed from a variety of materials, including but not limited to silicone, polyimide, polyethylene terephthalate, liquid crystal polymer, fluoropolymers such as polyvinylidene fluoride or polyvinylidene difluoride (PVDF), or materials similar to those under the commercial name of Tegaderm, or urethanes, polyurethanes, or thermoplastic polyurethanes. There can be multiple substrate layers. For example, between the substrate on which the electrodes are disposed and the skin, there can be a foam layer, optionally with cutouts at the electrode sites. Slits or openings can be added to one or more layers to allow the substrate to flex and stretch with the skin. The layer contacting the skin can have adhesive to strengthen the connection. For example, acrylate-based adhesive can be used. In some cases, it is not desirable to bond the device tightly to the skin with adhesive. For example, it may be desirable to more easily remove or reposition the electrode patch without excessive pulling or tearing of skin (of particular concern in delicate locations, in cases of burn, trauma, or other injuries or conditions, or in the very young or elderly), or removal of outer skin layers. A lesser adhesive can be used, or high tack materials, such as formulations of hydrogels or silicones which can reversibly attach to skin but still be easily peeled off without causing damage or discomfort. Adhesives or substrate materials that dissolve or change adhesive properties under exposure to water, light, or various chemicals can also be used. Various fixturing methods, such as bands or straps can also be used to aid in the fixation of the patch electrode to the body.

The substrate can optionally be flexible and conformable (or otherwise) designed to mechanically interface with the skin or target tissues.

In some embodiments, the electrodes and or substrate can be translucent or transparent to one or more wavelength ranges of light or electromagnetic energy. Visual transparency can be advantageous in the placement of electrode, for example based on underlying anatomic landmarks. It can also be advantageous to visualize or image the skin or tissue underlying the electrode array and/or substrate. In can also be advantageous to optically interact with the underlying tissue, for optical measurements/sensing/imaging, or for optical stimulation and delivery of electromagnetic energy. In some cases transparency to specific electromagnetic wavelengths, inside or outside the visible spectrum would be advantageous. For example, infrared based light emitters and/or sensors are able to stimulate/measure measurements through skin to detect biological properties. For example, vasculature can be imaged transcutaneously through IR means. Heart rate, blood oxygenation levels and other measurements can also be taken. Transparency to imaging modalities such as MRI or X-ray can in some cases be advantageous as well and materials selected for accordingly.

Energy may be delivered or measured from one or more electrodes acting in coordination. For example, current may be delivered to one or a multitude of electrodes together serving as the cathode. Patterns of current delivery can be distributed unequally between individual electrodes, varied in amplitude or with spatiotemporal patterns. Current delivery through single or multiple electrodes in coordination can enable strategic "steering of currents" towards target tissues. That is, through the modeling of the relevant tissues via finite element field models and possibly nerves via multicompartment axon models, it becomes possible to develop a source model that allows the specification of the desired current in a nerve segment. By solving the reverse model this specification becomes the desired applied current on each subcutaneous electrode. This methodology can be iterated and optimized to satisfy practical constraints (e.g., maximum acceptable electrode current densities). Multiple electrodes can be combined to form virtual electrodes.

In same embodiments, the patch can be disposable or meant to be applied for limited time or for a limited number of uses. In other cases, the patch can be designed for long term placement and/or reusability.

It can be advantageous for one or more of the electrodes to be positioned with high spatial precision in relation to each other and/or to underlying tissues. For example, it may be advantageous for one or more electrodes or groups of electrodes to be positioned directly over the target tissue. It is contemplated that electrodes or the electrode's substrate be movable and/or repositionable. For example, the patch/skin interface can be designed to enable sliding. Moving of the electrodes or patch can be manual, semi-automated, or fully automated through mechanical/robotic and/or software assistance.

Repositioning of the electrodes and/or patch and/or portions of the patch can be performed in conjunction with various types of feedback loops. For example, real time measurement through the electrodes might inform repositioning. Similarly, electrodes can deliver stimulations and measure the response to inform repositioning of the device. The response can be detected from electrodes on the same patch or on a different patch. For example, current can be delivered through one or more electrodes in one area of the patch in order to stimulate a nerve, while recording electrodes in another area of the patch measure the evoked signal within the same nerve. The stimulation electrodes can be physically adjusted based on the amplitude of the recorded nerve signal.

Stimulating electrodes can be designed to enable repositioning at any point without removal, or in other words, without spatial separation of the skin-to-electrode interface. For example, electrodes can be in the form of metal domes able to slide across the skin during repositioning. These electrodes can be connected to a mechanical structure to assist or automate in this repositioning. Advanced analysis algorithms from measurements from one or multiple electrodes can be used to interpret stimulation effects and inform physical repositioning and/or adjustment of individual currents to effect current steering. The system for moving electrodes can be configured such that the electrodes are strategically and efficiently moved. For example, one or more electrodes serving as the anode or virtual anode can be translated or rotated along an arc while the cathode position is held constant or translated/rotated within a tighter position over the known target area.

In some existing electrode arrays designed for electromyogram (EMG), a non-disposable circuit and electrode array is provided along with a disposable intermediate foam layer with holes cut out above the electrode sites. Conductive gel can be added to the holes to allow for low impedance skin/electrode contacting. Conductive gel is held in place by surface tension. The electrode patches described herein contemplate a different arrangement, in which the circuit and electrode array are provided with pre-attached hydrogel electrodes. The pre-fabricated nature of the device removes the need for intermediate steps. Device handling and application onto the skin are made easier by the attached hydrogel electrodes. The raised nature of the hydrogel electrodes improves electrode/skin contact for improved electrical interfacing with underlying structures. The foam sheet, or similar can have hydrogel electrodes already incorporated. In other words, as described above, the hydrogel is attached to the flexible substrate during manufacture.

In some cases, a non-disposable side of the circuit incorporates penetrating aspects in the design to make a connection with the backside of the penetrable electrodes (e.g. hydrogel) on the disposable side.

In some cases, especially when the connector pad region of the electrode patch is flexible, a connector can be designed where the connector pad region is pulled, instead of pushed into the mating connector. This can be accomplished by a permanent or temporary or sacrificial or separately attached pull tab.

For a functional advantage or to facilitate fabrication, gel based electrodes can be of different size or can be partially offset from an underlying conductive pad (e.g. screen printed Ag/AgCl pad). The gel/skin impedance is typically much higher than the impedance of the gel or gel to conductive pad impedance, so a medium resistivity gel can be used without reducing signal fidelity, and only a small area of the gel needs to overlap and make contact with an underlying conductive pad.

Traces and Vias

Various means of delivering and/or receiving energy as well as different materials choices throughout the design of the device are contemplated. Current can be delivered through conductive traces, for example composed of metal, conductive polymer, conductive silicone or similar materials. Electrical vias can serve to transmit current through layers of the device or from the bottom to the top of the substrate. In other embodiments, a portion of the substrate can be curled, folded, creased, or bent such that signals are routed to the top surface of the patch. In some cases, vias or other through-connections can be used to provide a direct connection to individual electrodes without trace routing.

Electrical signals can be transduced to light so that optical measurement can obviate the need for local traces and connections.

Connections

Direct contact can be made to the electrodes, eliminating the need for traces. For example, a penetrating aspect of a mating connector conductor can pierce the backside of the patch electrode to make direct contact with the electrode. Or an open window on the patch can expose the electrode for contact by a conductive connector member (or for visualization in the case of optical transduction). In a more conventional case, the electrode can be in direct continuity with a backside snap, as on typically ECG electrodes, where a trace is not necessary. These backside conductors can be miniaturized and arrayed through novel techniques to provide for direct connection with a mating connector.

In some cases a gel or conductive rubber or other conformable or penetrable material is used as a conductive pad for connection by a mating conductor. For example, the mating conductor can have one or more microneedles for penetrating and making a robust connection. Or the mating conductor can have pins or pads where pressure can be applied to deform a conformable pad on the patch side to make reliable connection.

Patch-electrode

In some implementations, electrodes and traces are electrically connected to the periphery where one or more groups of conductive pads connectors are located.

In some embodiments, a connector is important to interface the electrode patch with external electronics. In some cases, it is advantageous for the electrode patch to be manufacturable as inexpensively as possible. This might be the case, for example, when the electrode patch is designed to be disposable or designed to be used one or a few times. One inexpensive method of manufacture that enables connection is to have electrical traces extending from one or more electrodes to one or more conductive pads. The conductive pads can be located to the periphery of the device. In one embodiment, the electrode patch comprises an area of conductive pads, each connected by a separate trace to one electrode. Connectors can also be attached to the patch side of the electrode. In some cases, these connectors can be manufactured and assembled to the patch electrode cost-efficiently. Where conductive pads are mentioned in following descriptions, it is understood that with relatively little modification a patch side connector can also be used.

Clam-shell Type Connector, Patch-electrode Stiffener, Alignment Mechanisms

The patch-side conductive pads can be grouped in one or more areas to make connections with one or more mating connectors with conductive connections designed to make contact with each pad. In some cases, the mating connector can be designed to clamp like a clam shell on each side of the area of conductive pads, where a locking or clamping mechanism maintains a firm connection between the conductive pads and mating conductors. An example is shown in FIG. 11. The area of conductive pads can be shaped, or keyed in such a way to provide alignment with the mating conductor. For example, the area of conductive pads can have holes and the mating conductive can have guide pins or posts designed to mate with the holes and self align the circuit during clamping.

In some cases, where the one or more regions of conductive pads are otherwise be flexible, it can it be mechanically stiffened. For example, a secondary substrate can be attached underneath the area, or the area can be of increased thickness relative to other layers. Methods of stiffening a flexible circuit by having a secondary substrate attached are well known. The stiffened area of conductive pads can be designed to be inserted into a mating connector, again with conductors corresponding to the conductive pads. Such connection schemes are also well known. For example, zero insertion force, or ZIF connectors are common in consumer electronics. The mating connector can have conductors comprised of springs or spring loaded pins, in order to maintain connection with the conductive pads. In some cases the mating connector can close or clamp over the area of conductive pads, for example, by a lever. In some cases the flexible circuit and contact pads can be pushed into a crack or cavity on the connector side, using a tool, shaped for example like a credit card. This configuration can include a reversible locking mechanism that holds the flexible circuit in place until a release mechanism is actuated. In some configurations, spring loaded contact pins within a slot are provided on the connector side, and the stiffened circuit with contact pads is pushed onto this slot, sliding underneath the spring loaded contact pins, reminiscent of how a key slides underneath key pins in a pin tumbler lock cylinder.

Physical Guides, Aids in Connector Mating, Clamping

For some applications method of connection that is more durable, or more easily actuated would be advantageous. In one embodiment, area of conductive pads designed to be inserted into a connector can have a ferromagnetic component that assists and maintains the insertion. For example, the secondary stiffening substrate or a separate substrate can be a metal or ferromagnetic material, such as a stainless steel plate, to enable magnetic attraction to the mating connector.

A physical feature for gross/fine alignment can be included to aid in the positioning of the mating connector. This feature can also serve to maintain the connection. For example a snap or clasping post can be included in the vicinity of the pads to aid in alignment and also physically maintain the connection of the mated connectors. In some cases, metals or radio-opaque materials can be incompatible with techniques or equipment, such as X-ray or MRI. In these cases, ceramics, carbon based materials, or non-ferromagnetic materials can instead be used.

System-side Connector is Placed Down onto Patch Electrode-side Pads

In other embodiments, it would be advantageous for the one or more areas of conductive pads not to have to be inserted into the mating connector. It might be preferable, for example, for the mating connector to be directed down onto the conductive pads from above when making connection. For example, the mating connector can have conductors consisting of one or more spring loaded pins, designed to mate with the conductive pads on the electrode patch. In this embodiment, it may be preferable for there to be a means of guiding/aligning the proper physical placement of the mating connector so that mating conductors make precise alignment the conductive pads. These means can consist of one or more tapered guideposts, either on the patch electrode side or the mating conductor side.

The mating connector side can also have a cavity designed to match the outer dimensions of the area of conductors. This cavity can be tapered to facilitate the connection. One or more metallic, magnetic, or ferromagnetic, locations can also be provided on the patch electrode side or mating connector side to provide physical alignment, guidance in making the connection. An example is shown by FIG. 12. It can also be preferable for there to be a means of maintaining a firm physical connection between the mating connector and portion of the patch electrode containing conductive pads. In some cases, especially where there are many connections to be made, this required force can be substantial. One or more snaps, guideposts, clamping anchors, or spring-based mechanisms can be used to provide alignment as well as a source or force to maintain the connection. An example is shown by FIG. 13. Magnetic forces can also be used to maintain the connection. For example, a ferromagnetic substrate can be inexpensively attached to the area of conductors, to provide stiffening also attractive mating with the connector. Areas of ferromagnetic material can be placed to provide alignment and also a clamping force. The ferromagnetic material can be underneath the conductive pads or above the conductive pads, in a configuration such that the pads are still exposed for connection. For example, the ferromagnetic piece can have holes or openings matching the area of the conductive pads.

In cases where a spring-based movable contact is described for making stable electrical connection, it is understood that a static contact might instead be provided, but the conductive pad on the opposite side of the connection instead can move or compress to maintain contact. For example, instead of a spring loaded pin being provided on the connector side, a static pin can be provided, designed to compress a conductive rubber or gel pad. Friction fits can also be provided to maintain stable connections. For example a plastic housing, e.g. in a cylinder shape with keyed extrusion to maintain orientation, can have conductors provided around the outer circumference, and when this cylinder is press fit into a round hole on the opposite side, whereby the hole has conductors on its interior circumference, compression of the plastic housing can serve to maintain a friction fit between the connections.

In some of these embodiments, the electrodes in contact with the body are on the bottom-side of the patch array, but the conductive pads or connectors must be on top of the electrode array. Different types of electrical vias can serve to transmit current through layers of the device or from the bottom to the top of the substrate. Or, physical openings in the form of wells can be structured, from the top of the device to the bottom-side conductive pads. These openings can be created by a variety of means, including lasering, chemical etching, precision machining, or precision punching, In other embodiments, it can be more costly or difficult to include electrical vias or openings. One or more conductive clips or wires can be instead used at the edge of a part of the patch to make connections from the bottom to the top of the substrate. Alternatively, a portion of the patch can be curled, folded over, creased, or bent such that signals are routed to the top surface of the patch. An example is shown in FIGS. 14A and B. In some cases, a secondary substrate is provided around which the flexible circuit can be folded. This substrate can have a rounded, beveled, or bull-nosed edge to allow for the flexible circuit to fold over without creasing or at such a sharp angle that electrical traces crack, break, or otherwise become continuous. The secondary substrate can also provide stiffening, ferromagnetic attraction, or have integrated alignment features or physical locking/snapping/clasping/clamping to maintain connection with the mating connector. In some embodiments, the conductive pads are located on the bottom of the patch array and pins from the mating conductor penetrate through the substrate and optionally through the conductive pads to maintain connection.

The circuit can be folded over on itself or around an intermediate layer that can provide rigidity, be ferromagnetic, and/or have physical features for alignment and locking like a snap. The conductive pads can fold over to be flat, or can fold over and then bend up to create a feature substantially perpendicular to the plane of the electrodes and enabling connection to a mating connector. A stiffener can be a separate or same piece that the circuit wraps around. It is appreciated that wrapping the circuit from two opposite sides and bending both sides upwards around an optional stiffener will result in a "double sided" ZIF style mating region, with conductors on both sides for easy insertion or mating to a slotted socket with corresponding mating conductors. There can be purposefully arranged some "slack" as part of the curling, folding, or bending of the circuit, to provide strain relief or mechanical isolation of the electrode array from forces of cable tugging.

The circuit can be folded over from multiple sides to form a substantially planar or curved connector. An intermediate layer can provide rigidity or have a snap or similar member provided for mating.

In some cases, it is advantageous to provide strain-relief, such that physical forces applied at the site of the connector (e.g. tugging from a cable) do not cause motion of the electrodes relative to skin, or otherwise impact signal measurement or delivery. One mechanism for this is to have an area of traces, away from the electrode side, be fixed to the skin, with adhesive or ties, such that physical forces (e.g., tugging on a cable) pull on the site of fixation away from the electrode array site.

Impedance Reduction

A limiting factor, both for stimulation and measurement is the tissue/electrode impedance, as well as impedance of superficial biological tissue. Human skin, for example, is known to have high electrical impedance at frequencies of interest. The outer stratum corneum layer, for example, is thin but of high impedance. In some cases, well known methods of skin abrasion can be used to lessen impedance to some degree.

It is also contemplated that techniques of altering skin impedance can be used in conjunction with the present disclosure in order to improve system performance. For example, means of heating, ultrasonic or acoustic delivery, chemical delivery can all be used to alter impedance of the skin. Microneedles, such as on commercial "dermarollers" can also be used to reduce skin impedance. In some envisioned scenarios, these techniques can be applied locally, only at the site of each electrode, so that the rest of the area is not unnecessarily treated, and also to encourage spread of current through the skin towards the target tissue and discourage lateral flow of current. For example, microneedles can be provided on a patch that sticks in and is the removed before or after placement of the electrode patch. The microneedles can penetrate outer layers of skin only underneath each electrode, such as to reduce skin impedance only locally underneath each electrode.

In some cases, electrodes can have penetrating aspects (e.g. microneedles) designed to pass through one or more layers of skin in order to reduce impedance to measured or delivered currents. Conductive materials such as metal or conductive polymers can also be injected through the skin via a syringe for percutaneous by-passing of high impedance skin layers or for percutaneous access to target tissues. Similarly, these materials can be delivered via syringe to be fully subcutaneous and provide a low resistance pathways for electric currents at levels underneath the skin.

In previous work a dermal piercing (commonly used cosmetically) has been proposed as a means of more efficient stimulation through the skin with minimal invasiveness.

It is also to be understood that many aspects of the systems and methods described herein for transcutaneous application could also be applied subcutaneously, percutaneously, or at a level of deeper implantation.

Artifact Mitigation: Right Leg Electrode and Buffer Circuit and Artifact

A "Driven Right Leg Circuit" or DRL circuit is often added to biological signal amplifiers to reduce common-mode interference. The small circuits measured by biological signal amplifiers (e.g., EEG, EMG, ECG, and ENG circuits), measure small microvolt to millivolt signals. However, patient's body can act as an antenna, picking up electromagnetic interference including especially 50/60 Hz noise from power lines. In a conventional DRL circuit, "a right leg electrode" (bias electrode) is placed on the patient with impedance coupling to actively cancel the interference. The right leg electrode is actively driven to match the ground of the biological signal amplifier. The patient ground is effectively driven to match the ground of the recording circuitry, so that the patient ground and recording electronics ground do not oscillate with respect to each other due to environmental noise picked up by the patient.

However, delays in a typical dynamic system make conventional DRL circuits vulnerable to instabilities. Accordingly, system bandwidth must be reduced to avoid such instabilities.

In some embodiments of the system described herein, alterations to the typical driven right leg circuit are made (see e.g., the circuitry of FIG. 10A). As stimulation artifact minimization is one of the top priorities in electrophysiological studies, one permutation of the method described herein focuses on minimizing artifact. It has been observed that the driven right leg circuit electrode setup, which drives the body-ground level based on the recorded potential of the electrodes (for purpose of minimizing recorded environment noise) can introduce unwanted ringing effects in the recording, due to the stimulation. In order to minimize both noise and artifact ringing, the system described herein can begin stimulation with the driven electrode circuitry turned off, (so as to reduce artifact ringing), and within a short time of stimulation turn back on the driven electrode to minimize noise during the region of interest. Similarly, the high pass pole of input filters can be quickly shifted after the stimulation pulse, such that the impulse response of the filter does not spread into the recorded signal.

In another embodiment of the system, instead of the typical driven right leg circuit, a separate isolated circuit is used to provide a very-high impedance ground connection to the patient (see e.g., circuitry of FIG. 1), essentially leaving the patient floating instead of connected to the instrumentation ground. In this modified version, the data acquisition equipment ground is driven to match the potential of the patient. This altered setup strongly attenuates any common-mode mismatch as well as differential mismatches introduced in the reference electrode path, as this electrode is used as the high-impedance ground reference. This altered setup removes a strong limitation of the common right leg electrode design. This altered setup is a feed-forward path instead of a feedback one that includes the measuring amplifiers, and can thus provide a very wide bandwidth of attenuation (>1 MHz) instead of the narrow bandwidth commonly used with the traditional design that tends to be limited to power line frequency components (<200 Hz). This wider bandwidth allows us to attenuate the common mode components not only of environmental noise, but of the stimulus artifact.

Automated Physical or Virtual Moving of Anode to Minimize Artifact

It has been shown that recording with electrodes which create isopotential lines orthogonal to those created by the stimulation electrodes minimizes artifact in electrophysiological recordings. To achieve these desired effects, the electrode array can have individually addressable electrodes in order to allow operators to choose the most appropriately placed stimulating electrodes for artifact suppression. Furthermore, the array can be arranged in such a way to allow for an easy tuning of electric field lines while stimulating in the same area. For example, there may be a centrally located cathode with individually addressable anodes located in a concentric circle or arc around said cathode. Alternatively, there may be a centrally placed cathode and a single anode which is mobile about a concentric circle or arc surrounding said cathode. Aforementioned anode can be on a mechanism which allows easy tuning of anode position about an arc or circle surrounding the cathode.

In a further aspect, the system can be portable.

Algorithms, Firmware, Hardware

A variety of advanced and useful algorithms can be implemented using the systems and methods described herein. For example, the capacity for automation or semi-automation of electrical stimulation and recording paradigms is possible. For example, in the determination of optimal stimulation parameters, a variety of stimulation can be quickly and automatically delivered at low intensities during simultaneous measurement of evoked activity. Only after determining optimal stimulation patterns would "full strength" stimulation be used. This would make procedures less painful, which can be particularly important in situations where the patient is a child or infant.

Noise Reduction

In some cases measurement data will be evoked periodically. For example, a pair of stimulating electrodes at the middle finger can stimulate the distal median nerve at that location while a second set of measurement electrodes located on the surface of the wrist records propagated nerve activity associated with each stimulation. The same stimulation pattern can be delivered more than once such that multiple measurements of the same evoked signal are obtained. These two or more measurements can then be precisely time aligned and then averaged together, such that common signal is retained while random noise is averaged away. Noise will be increasingly averaged away with increasing number of samples. This technique is well known in the field as trigger-based averaging. Electronic methods for trigger-based averaging often include a precise digital trigger or timestamp generated by the stimulation electronics. This time marker can be used to synchronize the recording electronics to the stimulation pulse. In the case of digitized recordings, there will be a small amount of jitter sampling period. If the stimulus artifact is used as the synchronization pulse, then the time jitter between samples is based on the sampling period of the recordings.

In one embodiment of this system, the stimulation and recording electronics are operating off of the same clock, to provide for extremely precise synchronization between the stimulation and recording signals. In this case the "jitter" between stimulation and recording synchronization is within one clock cycle. Clock cycles in electronics can be in the megahertz range or higher, allowing for synchronization within one microsecond or less.

In another embodiment of the system, the recording electronics are not only precisely synchronized to the stimulation timing, but the stimulation timing itself is extremely precise. In typical scenarios, there is not a need for stimulation timing to be extremely precise, so long as recordings are precisely timed with the stimulation. For example, in nerve conduction studies, the nerves can be stimulated several times, approximately one second apart at the push of a button. In this system the timing of the stimulation is extremely precise, for example with microsecond precision or better. Thus, instead of stimulations being delivered every one second, stimulations can be delivered every 1.0000000 seconds. This precise stimulation timing enables several important capabilities. For example, two successive stimulations can be delivered precisely in phase or out of phase with other signals. For example, by sampling precisely in phase and out of phase with 60 Hz noise on successive samples, 60 Hz noise can be averaged out with as few as two stimulations.

In some cases, recording electronics have a fixed sampling frequency. For example a data acquisition chip can have an upper limit sampling frequency of F. In these cases, we describe a method to artificially increase the sampling frequency by including two chips in parallel, whereby a single electrode is attached to the recording inputs of both chips. In this case the clock controlling each chip is precisely timed and one chip samples at a ½ sample delay. Thus, a given electrode is sampled at time 0 by one chip, (1/F)/2 by a second chip, and then then 1/F by the first chip, and so on. This effectively doubles the achievable sampling frequency. The same process can be used with more chips with clocks precisely offset appropriately. Increasing sampling frequency allows an effective decrease in noise.

Software User Interface

A software-based user interface such as a graphical user interface would allow visualization of recorded signals, allowing on-the-fly analysis and, if necessary, adjustment of the electrode positioning, current delivery, signal processing, and other experimental parameters. The user interface can display "images" of recorded activity from underlying tissue. Anatomical structures including electroactive or non-electroactive tissues can be mapped and displayed in 2D or 3D. Instructions for manual repositioning of the electrodes or electrical setup can be provided to the operator. It is appreciated that the details of the software graphical user interface (GUI) can be specific to different applications. The user interface can instruct a patient to make an adjustment to his or her activities based electrode-based measurements. Or the interface can instruct the patient to make an adjustment to stimulation or recording electrodes based on a recorded physiological measurement. The interface can be based on software running on a desktop or laptop computer, on a tablet, or smaller or body worn computing device, such as a smart phone, or smart watch.

Applications

A high resolution electrode-array based device can enable advanced neurology or physiatry studies. High spatial-temporal resolution measured nerve signals can provide new capabilities for clinical measurement, screening and diagnostics. For example, local conduction velocities can be measured to indicate with higher spatiotemporal resolution for predictive, screening, or diagnostic information.

Functional nerve imaging allows visualization of the nerve and its branches and simultaneous assessment of nerve conduction for one or more nerves or branches. For example, the ring finger (innervated by both the median and ulnar nerve) can be stimulated while the patch measures activity separately and simultaneously from both the median and ulnar nerves. The median nerve travels through the carpal tunnel, and in cases of carpal tunnel syndrome can be compressed or effected such that the features of the nerve signal are affected. For example the conduction velocity of signals propagated through the nerve in the region of the carpal tunnel can be slowed relative to normal. The ulnar nerve does not travel through the carpal tunnel and would not experience compression or the resulting reduction in conduction velocity. Thus, a simultaneous measurement where the ulnar nerve propagates the signal much quicker than median nerve can indicate carpal tunnel syndrome.

The spatial information provided by a high-resolution array can also be used to distinguish among different nerve fibers inside a nerve. By using velocity-sensitive filtering also known as beamforming in the electrophysiology literature (i.e., differentially delaying and combining the signal from different electrodes), A$\alpha$, A$\beta$, A$\gamma$, A$\delta$, B, and C fibers that reside on the same nerve could be distinguished from each other as these groups of fibers have different conduction velocities. Likewise, afferent fibers and efferent fibers could be distinguished by the direction of propagation, allowing to clearly separate and classify stimulus responses from the different fibers carrying reflex and sensory information.

Structure information derived from imaging tissue activity via an electrode array can be informative to clinicians. Sonography based imaging and infrared light detection based imaging are examples of technologies used to detect the location of anatomical structures such as nerves or veins. In some cases, this existing measurement technology is then used to project an image of the underlying vasculature direction on the patient. For example, IR based imaging is relatively simple and cheap, and can be used to identify superficial blood vessels to aid with the insertion of needles (e.g. IV insertions or blood draws). Measurements of tissue activity could similarly be used to inform patients or clinicians or to similarly project a superimposed image of, say, a nerve on the proper location on a patient's arm.

Existing imaging technologies such as ultrasound or IR based imaging can also be used to inform the placement of the patch. Because many target nerves often travel along with blood vessels, this type of technology could be useful in in informing the placement of the patch. The more reliable the anatomical placement of the device, the less spatial coverage is required by an electrode or electrode array. Thus the patch and/or electrodes can be made smaller, or a given number of electrodes could be strategically arrayed more densely into a smaller area for higher spatial resolution of recording and/or stimulation.

Informing Optimal Treatment

High resolution, fine quantitative assessments of nerve or muscle function could also improve current diagnostic capabilities and help to inform optimal treatment. For example, in the surgical treatment of carpal tunnel syndrome two decompression techniques are often used: (1) open carpal tunnel release, a traditional invasive surgery, as well as (2) an endoscopic carpal tunnel release, a minimally invasive alternative, which has a shorter recovery time, but a reduced success rate (Kim, 2014).

Neuropathy as an End Point for Safety Testing

Another case where advanced means of measuring nerve activity is important is for measuring the therapeutic effects or side effects of drugs. Measurement from autonomic innervation sites or epidermal nerve fibers is often neglected in diagnostic testing. The sensitive, array-based device described herein, and algorithms for artifact and noise reduction make the system uniquely enabled to perform measurements in these types of challenging scenarios.

Intra-operative Neural Monitoring

Intra-operative neural monitoring (IONM) is used to reduce the risk of nerve damage to patients undergoing sensitive and invasive procedures involving the brain and spinal cord. During these procedures, there are three primary methodologies that use electrodes to stimulate and record the time it takes for the electrical signal to travel: Somatosensory Evoked Potentials (SSEP), Transcranial Motor-Evoked Potentials (TcMEP) and Electromyography (EMG). Using a plurality of electrodes, IONM may be improved and used on nerves which are typically harder to record from but may be more clinically relevant.

On-target Stimulation and Supporting Algorithms

Neuromodulation, bioelectronic medicine, stimulation to treat various conditions, pain, or disease can involve stimulation of electroactive tissues, via electrical, magnetic, optical, electromagnetic (e.g. near infrared light), ultrasonic, acoustic, mechanical (e.g. acupuncture or pressure) and other means. For example, various means are used to directly or indirectly stimulate autonomic nerves, such as the vagus nerve or its collaterals, in order to relieve various conditions. Motor/sensory nerves can be stimulated e.g. with TENS (transcutaneous electrical nerve stimulation) or with devices designed to block nerve activity. In many cases, it can be difficult to known whether the stimulation is "on target" and indeed affected the desired target nerve. A sensitive, reliable, and robust means of measuring evoked nerve or muscle activity would provide useful feedback on whether the stimulation is having the desired effect and/or how the stimulation might be adjusted to achieve or optimize a desired effect.

Alternatively, one variation of the systems and methods described herein is tracking on and off target stimulation for surface stimulators including, but not limited to, transcutaneous electrical nerve stimulation (TENS) devices. TENS devices target specific nerves typically in order to minimize pain. The device discussed herein can be used to determine whether the corresponding TENS device is stimulating the correct nerve so as to optimize efficacy of TENS device placement and improve patient quality of life.

It is known that transcutaneous recordings of underlying vagal nerve activity can provide useful feedback in the treatment of various conditions or diseases. For example, patterns of nerve activity can indicate efficacy of implanted stimulators. An transcutaneous electrode array would increase the resolution of these measurements.

One possible application of the array described herein includes recording from nerves that are close to the skin surface but innervate internal organs, which are in turn stimulated with implanted stimulators. One such example is recording from the vagus nerve at the neck while stimulating the stomach with a gastric stimulator. In this way, one may assess the efficacy of implanted stimulators and whether the target nerve (in this example, the vagus) is being stimulated effectively by the implanted stimulator.

In another example the vagus nerve can be stimulated in the neck and also measured from to understand what fiber populations may have been stimulated and to what degree. This feedback information could be used to updated the stimulation patterns. Similarly, vagal nerve stimulation can be stimulated/measured in different locations suitable for transcutaneous measurement, such as the ear.

Similarly it is known that transcutaneous recordings can be used to detect and quantify changes in sympathetic nerve activity. For example, skin sympathetic nerve activity (SKNA) can be measured with a large, conventional EKG style electrode to gauge sympathetic nerve activity or sympathetic tone, which can be a useful physiological metric, for example as a predictive measure of cardiac arrhythmias. The sensitive and robust electrode array based platform described herein with specialized electrodes allows more practical implementation of these recordings, and increased sensitivity and spatial resolution to increase analysis. It has been shown for the first time that this signal can be detected from miniaturized or array based electrodes through the skin, yielding the possibility for enhanced analysis and investigation of spatial information such as directionality and spatial mapping of the underlying signal.

Features for Clinical Use

The sensitivity, robust nature of an array-based system, and capabilities for automation or feedback to the operator allows clinicians or other health care providers with less specialized training or experience to administer screenings, diagnostics or therapies. For example, various types of stimulation or operant conditioning protocols can help patients overcome effects after neuromuscular injuries or disease. Often these sessions take place in repeated sessions and are administered by less-experienced operators.

Features for At-Home Use

Similarly, it is often desirable for an individual to be stimulated or measured from at home in settings where a trained operator is not necessarily present. In this case sensitivity, robustness, and capabilities for automation or semi-automation are particularly crucial. Adaptive and "smart" software algorithms and an intuitive user interface are also critical in these settings.

Longitudinal Tracking

Longitudinal tracking here refers to periodic assessment of biological state or function nerve or muscle health over multiple interrogation sessions. Provide herein is an array with a plurality of electrodes that can, as one of many applications, monitor the post-surgical progress of the regenerating axons at high spatial resolution with repeatable results. As muscle and nerve health may be assessed via aforementioned electrode patch, and the array-based nature of aforementioned electrode patch allows for more replicable placement of electrodes over the target nerve, the systems and methods described herein allows for replicable electrode placement and therefore recordings which are comparable across different recording sessions. In this way, clinicians can compare consecutively recorded data and determine how a patient's nerve or muscle health changes over time.

In this way, one possible application for aforementioned electrode patch is to assess regeneration of a nerve posttransection or post-surgery. The investigator may place the electrode patch over a section of nerve distal to the site of injury or surgery, and assess the location and constitution (e.g. axonal composition such as fiber type, size, degree of myelination, etc.) of the regenerating nerve front, based on analysis of electrode patch measurements. The array based nature of the device enhances capabilities for registration, for enhanced precision and sensitivity to changes from session to session. In some cases activity may be evoked, either volitionally from the patient or via induced means such as electrical stimulation of the affected nerve. Patch electrode-based precision delivery of current to target tissues can minimize stimulation of undesired nerves or tissues and minimize stimulation artifact, for enhanced sensitivity and precision. On the side of measurement, signal acquisition, signal conditioning, and analysis side, using techniques disclosed herein (e.g. array-based analysis, reduction of stimulation artifact, minimization of environmental and biological noise, enhanced registration, and precision trigger-based averaging) the patch-electrode based system will allow high sensitivity to small biological signals associated with the regenerating nerve front, the capture of which would be otherwise intractable. Similarly the systems and methods described herein can be used for fine assessment of the degree of neuromuscular function, e.g. as a measure of reinnervation be regenerating axons. Signals from nerve, muscles, and reflex pathways can all be used for these assessments, which can also inform the progression of a disease or other pathology or amelioration via treatment, therapy, or natural healing. Enhanced characterization of neuromuscular function in this way can provide more sensitive and discriminating quantitative measures to better inform intervention.

The array-based and sensitive nature of our system enable interfacing with epidermal nerves which are typically neglected in diagnostic testing. Sensitive, longitudinal measurements of these fine nerves over time, for example, can be used to diagnose or track progression of disease or injury.

Multiple Sclerosis

The ability of the electrode arrays described herein to measure local changes in signal conduction could be valuable in the diagnosis, or treatment of Multiple Sclerosis (MS). In MS, local portions of the nerve can be affected, introducing focal slowings, reduced transmission, or complete conduction block. The patches can be used to localize these affected areas with spatial precision, and track the function of an affected area over time.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system comprising:
   at least one electrode patch configured to be removably secured to a skin of a subject for at least one of delivering a stimulus to an electroactive tissue or recording an evoked electrical response from the electroactive tissue; and
   electronic circuitry operably coupled to the at least one electrode patch and configured to:
   deliver, via the at least one electrode patch, successive stimuli to the electroactive tissue with precise timing;
   record, via the at least one electrode patch, the evoked electrical response from the electroactive tissue; and
   remove noise at a given frequency from the evoked electrical response by averaging successive samples of the evoked electrical response that correspond to the successive stimuli, where to record the evoked electrical response from the electroactive tissue, the electronic circuitry is configured to deliver one or more first stimuli of the successive stimuli in-phase with the noise at the given frequency and one or more second stimuli of the successive stimuli out-of-phase with the noise at the given frequency, the one or more second stimuli of the successive stimuli being shifted by at least a fraction of a cycle relative to the noise at the given frequency, wherein averaging the successive samples of the evoked electrical response comprises averaging evoked electrical responses to the successive stimuli.

2. The system of claim 1, wherein the at least one electrode patch comprises a plurality of independently addressable electrodes arranged in a grid.

3. The system of claim 2, wherein each independently addressable electrode comprises a hydrogel having a raised geometry that causes the hydrogel to extend beyond a distal-most plane of the at least one electrode patch such that the hydrogel is configured to be in direct and uninterrupted contact with the skin of the subject.

4. The system of claim 1, wherein the electronic circuitry is further configured to adjust a stimulus delivered to the electroactive tissue based on the evoked electrical response.

5. The system of claim 1, wherein the noise at the given frequency is 50 Hz or 60 Hz noise caused by electromagnetic interference from power lines.

6. The system of claim 1, wherein the electronic circuitry comprises a driven right-leg circuit configured to:
   measure a common-mode of the subject; and
   force a ground of the electronic circuitry to the common-mode.

7. The system of claim 1, wherein the electronic circuitry comprises a first processing chip and a second processing chip operably coupled to the at least one electrode patch, each of the first processing chip and the second processing chip configured to record the evoked electrical response from the electroactive tissue, wherein the second processing chip records the evoked electrical response from the electroactive tissue with a half-sample delay with respect to the first processing chip.

8. The system of claim 1, further comprising a compression pad configured to apply pressure to the at least one electrode patch.

9. The system of claim 8, wherein the at least one electrode patch comprises a plurality of independently addressable electrodes arranged in a grid, wherein the compression pad comprises a plurality of rigid members corresponding to each of the plurality of independently addressable electrodes, and wherein each of the plurality of rigid members is configured to focus the pressure onto a respective one of the plurality of independently addressable electrodes.

10. The system of claim 1, wherein the system comprises a plurality of electrode patches including the at least one electrode patch, each of the plurality of electrode patches being configured to be removably secured to the skin of the subject for at least one of delivering the stimulus to the electroactive tissue or recording the evoked electrical response from the electroactive tissue, wherein the electronic circuitry is further configured to deliver, via one or more of the plurality of electrode patches, successive stimuli to the electroactive tissue with precise timing, and record, via one or more of the plurality of electrode patches, the evoked electrical response from the electroactive tissue.

11. The system of claim 1, wherein the electronic circuitry is configured to synchronize delivery of the successive stimuli and recordation of the evoked electrical response using a same clock.

12. The system of claim 11, wherein the electronic circuitry is configured to synchronize delivery of the successive stimuli and recordation of the evoked electrical response within one cycle of the same clock.

13. A system comprising:

a plurality of electrode patches, each of the plurality of electrode patches being configured to be removably secured to a skin of a subject for at least one of delivering a stimulus to an electroactive tissue or recording an evoked electrical response from the electroactive tissue; and electronic circuitry operably coupled to the plurality of electrode patches and configured to:

deliver, via one or more of the plurality of electrode patches, successive stimuli to the electroactive tissue with precise timing;

record, via one or more of the plurality of electrode patches, the evoked electrical response from the electroactive tissue; and remove noise at a given frequency from the evoked electrical response by averaging successive samples of the evoked electrical response that correspond to the successive stimuli, where to record the evoked electrical response from the electroactive tissue, the electronic circuitry is configured to deliver one or more first stimuli of the successive stimuli in-phase with the noise at the given frequency and one or more second stimuli of the successive stimuli out-of-phase with the noise at the given frequency, the one or more second stimuli of the successive stimuli being shifted by at least a fraction of a cycle relative to the noise at the given frequency, wherein averaging the successive samples of the evoked electrical response comprises averaging evoked electrical responses to the successive stimuli.

14. A system comprising:

at least one electrode patch configured to be removably secured to a skin of a subject for at least one of delivering a stimulus to an electroactive tissue or recording an evoked electrical response from the electroactive tissue; and electronic circuitry comprising a single synchronization clock, the electronic circuitry being operably coupled to the at least one electrode patch and configured to:

deliver, via the at least one electrode patch, successive stimuli to the electroactive tissue with precise timing using the single synchronization clock;

record, via the at least one electrode patch, the evoked electrical response from the electroactive tissue with precise timing using the single synchronization clock, wherein delivery of the successive stimuli and recordation of the evoked electrical response are synchronized within one clock cycle of the single synchronization clock; and remove noise from the evoked electrical response by averaging successive samples of the evoked electrical response that correspond to the successive stimuli.

15. A system comprising:

a plurality of electrode patches, each of the plurality of electrode patches being configured to be removably secured to a skin of a subject for at least one of delivering a stimulus to an electroactive tissue or recording an evoked electrical response from the electroactive tissue; and electronic circuitry comprising a single synchronization clock, the electronic circuitry being operably coupled to the plurality of electrode patches and configured to:

deliver, via one or more of the plurality of electrode patches, successive stimuli to the electroactive tissue with precise timing using the single synchronization clock;

record, via one or more of the plurality of electrode patches, the evoked electrical response from the electroactive tissue with precise timing using the single synchronization clock, wherein delivery of the successive stimuli and recordation of the evoked electrical response are synchronized within one clock cycle of the single synchronization clock; and remove noise from the evoked electrical response by averaging successive samples of the evoked electrical response that correspond to the successive stimuli.

* * * * *